United States Patent
Stand et al.

(10) Patent No.: US 10,238,460 B2
(45) Date of Patent: Mar. 26, 2019

(54) HIGHLY ARTICULATED ROBOTIC PROBES AND METHODS OF PRODUCTION AND USE OF SUCH PROBES

(71) Applicant: Medrobotics Corporation, Raynham, MA (US)

(72) Inventors: Joseph A. Stand, Holden, MA (US); Robert A. Didomenico, Norfolk, MA (US); Brett Zubiate, Pittsburgh, PA (US); Ian J. Darisse, Allston, MA (US); J. Christopher Flaherty, Auburndale, FL (US)

(73) Assignee: MEDROBOTICS CORPORATION, Raynham, MA (US)

( * ) Notice: Subject to any disclaimer, the term of this patent is extended or adjusted under 35 U.S.C. 154(b) by 0 days.

(21) Appl. No.: 14/587,166

(22) Filed: Dec. 31, 2014

(65) Prior Publication Data
US 2015/0313449 A1 Nov. 5, 2015

Related U.S. Application Data

(63) Continuation of application No. 13/880,525, filed as application No. PCT/US2011/057282 on Oct. 21, 2011, now Pat. No. 8,992,421.
(Continued)

(51) Int. Cl.
*A61B 1/00* (2006.01)
*A61B 34/00* (2016.01)
(Continued)

(52) U.S. Cl.
CPC ............ *A61B 34/71* (2016.02); *A61B 1/0055* (2013.01); *A61B 1/0057* (2013.01); *A61B 34/30* (2016.02);
(Continued)

(58) Field of Classification Search
USPC .................................................. 600/139–142
See application file for complete search history.

(56) References Cited

U.S. PATENT DOCUMENTS 2,510,198 A * 6/1950 Tesmer .................. B23Q 1/285
248/160
3,060,972 A 10/1962 Sheldon
(Continued)

FOREIGN PATENT DOCUMENTS

EP 0653922 11/2005
EP 1015068 9/2011
(Continued)

OTHER PUBLICATIONS

Examiner's Report dated Oct. 1, 2015 in corresponding Australian Patent Application No. 2011316849.
(Continued)

*Primary Examiner* — Matthew J Kasztejna
(74) *Attorney, Agent, or Firm* — Onello & Mello, LLP

(57) ABSTRACT

A highly articulated robotic probe comprises an outer sleeve and an inner core. The outer sleeve and inner core include a plurality of links. The links of the outer sleeve and inner core are configured to pivot relative to one another. Various characteristics of the links determine the overall pivot angle of the articulated probe. Each of the plurality of links may have one or more channels. The channels form a semi-continuous passage from link to link and are configured to receive an elongated member such as an inner core, tool or cable. One or more cables may be used to control the outer links of the outer sleeve and the inner links of the inner core. Various characteristics of the cables determine the overall performance of the articulated probe.

27 Claims, 26 Drawing Sheets

Related U.S. Application Data

(60) Provisional application No. 61/406,032, filed on Oct. 22, 2010.

(51) Int. Cl.
  *A61B 1/005* (2006.01)
  *A61B 34/30* (2016.01)
  *A61B 1/018* (2006.01)

(52) U.S. Cl.
  CPC ......... *A61B 1/018* (2013.01); *A61B 2034/306* (2016.02)

(56) References Cited

U.S. PATENT DOCUMENTS

| | | |
|---|---|---|
| 3,557,780 A | 1/1971 | Sato |
| 3,572,325 A | 3/1971 | Bazell et al. |
| 3,583,393 A | 6/1971 | Takahashi |
| 3,625,200 A | 12/1971 | Muller |
| 3,638,973 A | 2/1972 | Poletti |
| 3,643,653 A | 2/1972 | Takahashi et al. |
| 3,703,968 A | 11/1972 | Uhrich et al. |
| 3,739,770 A | 6/1973 | Mori |
| 3,790,002 A | 2/1974 | Germond et al. |
| 3,892,228 A | 7/1975 | Mitsui |
| 3,920,972 A | 11/1975 | Corwin, Jr. et al. |
| 4,078,670 A | 3/1978 | Francois et al. |
| 4,108,211 A | 8/1978 | Tanaka |
| 4,150,329 A | 4/1979 | Dahlstrom |
| 4,221,997 A | 9/1980 | Flemming |
| 4,259,876 A | 4/1981 | Belyanin et al. |
| 4,260,319 A | 4/1981 | Motoda et al. |
| 4,299,533 A | 11/1981 | Ohnaka |
| 4,351,323 A | 9/1982 | Ouchi et al. |
| 4,432,349 A | 2/1984 | Oshiro |
| 4,445,184 A | 4/1984 | Noguchi |
| 4,474,174 A | 10/1984 | Petruzzi |
| 4,475,375 A | 10/1984 | Hill |
| 4,479,914 A | 10/1984 | Baumrucker |
| 4,494,417 A | 1/1985 | Larson et al. |
| 4,496,278 A | 1/1985 | Kaise |
| 4,502,830 A | 3/1985 | Inaba et al. |
| 4,517,963 A | 5/1985 | Michel |
| 4,531,885 A | 7/1985 | Molaug |
| 4,535,207 A | 8/1985 | Lindqvist |
| 4,564,179 A | 1/1986 | Hollingsworth |
| 4,600,355 A | 7/1986 | Johnson |
| 4,655,257 A | 4/1987 | Iwashita |
| 4,661,032 A | 4/1987 | Arai |
| 4,666,366 A | 5/1987 | Davis |
| 4,700,693 A | 10/1987 | Lia et al. |
| 4,706,001 A | 11/1987 | Nakashima et al. |
| 4,726,355 A | 2/1988 | Okada |
| 4,780,045 A | 10/1988 | Akeel et al. |
| 4,787,369 A | 11/1988 | Allred, III et al. |
| 4,790,294 A | 12/1988 | Allred, III et al. |
| 4,796,607 A | 1/1989 | Allred, III et al. |
| 4,804,897 A | 2/1989 | Gordon et al. |
| 4,805,477 A | 2/1989 | Akeel |
| 4,806,066 A | 2/1989 | Rhodes et al. |
| 4,830,569 A | 5/1989 | Jannborg |
| 4,831,547 A | 5/1989 | Ishiguro et al. |
| 4,838,859 A | 6/1989 | Strassmann |
| 4,863,133 A | 9/1989 | Bonnell |
| 4,864,888 A | 9/1989 | Iwata |
| 4,873,965 A | 10/1989 | Danieli |
| 4,888,708 A | 12/1989 | Brantmark et al. |
| 4,900,218 A | 2/1990 | Sutherland |
| 4,941,457 A | 7/1990 | Hasegawa |
| 4,943,296 A | 7/1990 | Funakubo et al. |
| 4,947,827 A | 8/1990 | Opie et al. |
| 4,949,927 A | 8/1990 | Madocks et al. |
| 4,950,116 A | 8/1990 | Nishida |
| 4,956,790 A | 9/1990 | Tsuchihashi et al. |
| 4,979,949 A | 12/1990 | Matsen, III et al. |
| 4,998,916 A | 3/1991 | Hammerslag et al. |
| 5,005,558 A | 4/1991 | Aomori |
| 5,006,035 A | 4/1991 | Nakashima et al. |
| 5,012,169 A | 4/1991 | Ono et al. |
| 5,037,391 A | 8/1991 | Hammerslag et al. |
| 5,044,063 A | 9/1991 | Voellmer |
| 5,046,375 A | 9/1991 | Salisbury, Jr. et al. |
| 5,064,340 A | 11/1991 | Genov et al. |
| 5,078,140 A | 1/1992 | Kwoh |
| 5,086,401 A | 2/1992 | Glassman et al. |
| 5,105,819 A | 4/1992 | Wollschlager et al. |
| 5,108,368 A | 4/1992 | Hammerslag et al. |
| 5,143,475 A | 9/1992 | Chikama |
| 5,167,221 A | 12/1992 | Chikama |
| 5,174,277 A | 12/1992 | Matsumaru |
| 5,176,126 A | 1/1993 | Chikama |
| 5,178,129 A | 1/1993 | Chikama et al. |
| 5,179,935 A | 1/1993 | Miyagi |
| 5,180,276 A | 1/1993 | Hendrickson |
| 5,193,963 A | 3/1993 | McAffee et al. |
| 5,195,968 A | 4/1993 | Lundquist et al. |
| 5,200,679 A | 4/1993 | Graham |
| 5,201,325 A | 4/1993 | McEwen et al. |
| 5,203,380 A | 4/1993 | Chikama |
| 5,203,772 A | 4/1993 | Hammerslag et al. |
| 5,217,003 A | 6/1993 | Wilk |
| 5,217,453 A | 6/1993 | Wilk |
| 5,236,432 A | 8/1993 | Matsen, III et al. |
| 5,251,611 A | 10/1993 | Zehel et al. |
| 5,254,088 A | 10/1993 | Lundquist et al. |
| 5,257,669 A | 11/1993 | Kerley et al. |
| 5,266,875 A | 11/1993 | Slotine et al. |
| 5,271,381 A | 12/1993 | Ailinger et al. |
| 5,297,443 A | 3/1994 | Wentz |
| 5,318,526 A | 6/1994 | Cohen |
| 5,327,905 A | 7/1994 | Avitall |
| 5,337,732 A | 8/1994 | Grundfest et al. |
| 5,386,741 A | 2/1995 | Rennex |
| 5,448,989 A | 10/1995 | Heckele |
| 5,524,180 A | 6/1996 | Wang et al. |
| 5,759,151 A | 6/1998 | Sturges |
| 5,899,425 A * | 5/1999 | Corey, Jr. ............ A61B 17/02 248/276.1 |
| 5,916,147 A * | 6/1999 | Boury ............... A61M 25/0147 600/139 |
| 6,080,181 A | 6/2000 | Jensen et al. |
| 6,132,368 A | 10/2000 | Cooper |
| 6,210,337 B1 | 4/2001 | Dunham et al. |
| 6,223,100 B1 | 4/2001 | Green |
| 6,234,958 B1 | 5/2001 | Snoke et al. |
| 6,346,072 B1 | 2/2002 | Cooper |
| 6,440,061 B1 | 8/2002 | Wenner et al. |
| 6,450,948 B1 | 9/2002 | Matsuura et al. |
| 6,743,239 B1 | 6/2004 | Kuehn et al. |
| 6,837,846 B2 | 1/2005 | jaffe et al. |
| 6,837,847 B2 | 1/2005 | Ewers et al. |
| 6,916,306 B1 | 7/2005 | Jenkins et al. |
| 7,182,764 B2 | 2/2007 | Jenkins et al. |
| 7,250,027 B2 * | 7/2007 | Barry .................. A61B 1/0056 600/139 |
| 7,789,875 B2 | 9/2010 | Brock et al. |
| 7,850,642 B2 | 12/2010 | Moll et al. |
| 7,854,109 B2 | 12/2010 | Zubiate et al. |
| 7,854,738 B2 | 12/2010 | Lee et al. |
| 7,867,241 B2 | 1/2011 | Brock et al. |
| 7,918,845 B2 | 4/2011 | Saadat et al. |
| 7,946,546 B2 | 5/2011 | Zubiate et al. |
| 8,075,476 B2 | 12/2011 | Vargas |
| 8,100,031 B2 | 1/2012 | Zubiate et al. |
| 8,192,422 B2 | 6/2012 | Zubiate et al. |
| 8,459,138 B2 | 6/2013 | Zubiate et al. |
| 8,465,420 B2 * | 6/2013 | Ostrovsky .......... A61B 1/00071 600/121 |
| 8,763,877 B2 * | 7/2014 | Schall .................. A61B 90/92 227/176.1 |
| 8,945,096 B2 | 2/2015 | Zubiate et al. |
| 9,011,318 B2 | 4/2015 | Choset et al. |
| 2001/0013764 A1 | 8/2001 | Blumenkranz et al. |
| 2002/0133174 A1 | 9/2002 | Charles et al. |

(56) References Cited

U.S. PATENT DOCUMENTS

| | | |
|---|---|---|
| 2002/0161281 A1 | 10/2002 | Jaffe et al. |
| 2003/0135203 A1 | 7/2003 | Wang et al. |
| 2004/0138529 A1 | 7/2004 | Wiltshire et al. |
| 2004/0193146 A1 | 9/2004 | Lee et al. |
| 2005/0033287 A1 | 2/2005 | Sra |
| 2005/0065397 A1 | 3/2005 | Saadat et al. |
| 2005/0090811 A1 | 4/2005 | Doyle et al. |
| 2005/0113640 A1 | 5/2005 | Saadat et al. |
| 2005/0215992 A1 | 9/2005 | Jenkins et al. |
| 2005/0216033 A1 | 9/2005 | Lee et al. |
| 2006/0052664 A1 | 3/2006 | Julian et al. |
| 2007/0299387 A1 | 12/2007 | Williams et al. |
| 2008/0027279 A1 | 1/2008 | Abou El Kheir |
| 2008/0119868 A1 | 5/2008 | Sharp et al. |
| 2008/0163603 A1 | 7/2008 | Zubiate et al. |
| 2008/0188869 A1 | 8/2008 | Weitzner et al. |
| 2008/0245173 A1 | 10/2008 | Schwerin et al. |
| 2009/0030428 A1 | 1/2009 | Omori et al. |
| 2009/0171151 A1 | 7/2009 | Choset et al. |
| 2009/0326556 A1 | 12/2009 | Diolaiti et al. |
| 2010/0022825 A1 | 1/2010 | Yoshie |
| 2010/0160735 A1 | 6/2010 | Bakos |
| 2010/0160736 A1 | 6/2010 | Padget et al. |
| 2010/0204713 A1 | 8/2010 | Ruiz Morales |
| 2010/0224022 A1 | 9/2010 | Choi et al. |
| 2010/0280325 A1 | 11/2010 | Ibrahim et al. |
| 2011/0028790 A1 | 2/2011 | Farr et al. |
| 2011/0056320 A1 | 3/2011 | Zubiate et al. |
| 2011/0152613 A1 | 6/2011 | Zubiate et al. |
| 2011/0184241 A1 | 7/2011 | Zubiate et al. |
| 2011/0213384 A1 | 9/2011 | Jeong |
| 2011/0313243 A1 | 12/2011 | Zubiate et al. |
| 2012/0209073 A1 | 8/2012 | McWeeney et al. |
| 2013/0091974 A1 | 4/2013 | Riwan et al. |
| 2013/0150673 A1 | 6/2013 | Kakehashi |
| 2014/0088356 A1 | 3/2014 | Matsuo et al. |
| 2016/0167223 A1 | 6/2016 | Zubiate et al. |

FOREIGN PATENT DOCUMENTS

| | | |
|---|---|---|
| JP | H04194406 | 7/1992 |
| JP | 2008504072 | 2/2008 |
| JP | 2013527041 | 6/2013 |
| WO | 2006073581 | 7/2006 |
| WO | 2009149421 | 12/2009 |
| WO | 201050771 | 5/2010 |

OTHER PUBLICATIONS

PCT ISRWO dated May 19, 2014, issued in International application No. PCT/US2014/010808.

Expo-70 Robot—Vadim Matskevich's students, http://cyberneticzoo.com/wp-content/uploads/2010/03/Expo-70-MK-1969-02-p31-3.pdf, 1969.

Conductor Robot, http://cyberneticzoo.com/wp-content/uploads/2010/03/Ticket-robot-russian-1973.pdf, 1973.

Michael L. Rhodes, "Computer Graphics and an Interactive Stereotactic System for CT-Aided Neurosurgery", IEEE Computer Graphics and Application, Computer Graphics in Medicine & Biology, 1983, p. 31-37.

Lee E. Weiss, Arthur C. Sanderson, Charles P. Neuman, "Dynamic Sensor Based Control of Robots with Visual Feedback", IEEE Journal of Robotics and Automation, 1987, p. 404-417.

Jean-Jacques E. Slotine, Weiping Li, "Composite adaptive control of robot manipulators", Automatica; Nonlinear Systems Laboratory, Massachusetts Institute of Technology, Cambridge, MA 02139, U.S.A., 1989, p. 509-519.

Weiping Li, Jean-Jacques E. Slotine, "An indirect adaptive robot controller", Systems & Control Letters; Nonlinear Systems Laboratory, Massachusetts Institute of Technology Cambridge, MA 02139, U.S.A., 1989, p. 259-266.

Xu Hongbin, "Stability and performance robustness analysis of hybrid control for robot manipulators", Journal of UEST of China, vol. 22 No. 5, Oct. 1993, p. 501-505.

Francois Chaumette, Patrick Rives, Bernard Espiau, "Positioning of a Robot With Respect to an Object, Tracking It and Estimating Its Velocity by Visual Servoing", IEEE International Conf. on Robotics and Automation, 1991, p. 2248-2253.

A.V. Timofejev, N.V. Ivanova, "Expert System of the Control Programs Designing of Adaptive Robots", The Lenigrand Institute of Aircraft Instrumentation, 1991, p. 912-915.

W Szczepiński, "Theory of polyhedrons of positioning accuracy of manipulators", Mechanism and Machine Theory; Institute of Fundamental Technological Research, Polish Academy of Sciences, 00-049 Warsaw, Swietokrzyska 21, Poland, 1991, p. 697-709.

Junji Furusho, Hiroshi Nagao, Naruse Makoto, "Multivariable Root Loci of Control Systems of Robot Manipulators with Flexible Driving Systems* : Distortion Feedback ", JSME International Journal, 1992, p. 65-73.

Potemkin, E., Astafurov, P., Osipov, A., Malenkov, M., Mishkinyuk, V., Sologub, P., "Remote-controlled robots for repair and recovery in the zones of high radiation levels", Robotics and Automation, IEEE, 1992, p. 80-82.

S. L. Shishkin, "Adaptive control of a biped robot walking across a horizontal plane", International Journal of Adaptive Control and Signal Processing, 1992, p. 259-264.

Henk Nijmeijer, "Global regulation of robots using only position measurements", Systems and Control Letters; Department of Electrical Engineering, Mechatronics Research Centre Twente, University of Twente, P.O. Box 217, 7500 AE Enschede, Netherlands, 1992, p. 289-293.

Hitoshi Maekawa, Kazuhito Yokoi, Kazuo Tanie, Makoto Kaneko, Nobuo Kimura, Nobuaki Imamura, "Development of a three-fingered robot hand with stiffness control capability", Mechatronics; Mechanical Engineering Laboratory, 1992, p. 483-494.

J.D. Moon, D.W. Cho, "A component mode synthesis applied to mechanisms for an investigation of vibration", Journal of Sound and Vibration; Department of Mechanical Engineering, Pohang Institute of Science and Technology, Pohang, Korea, 1992, p. 67-79.

Timopheev, A.V., Prokhorov, D.V., "Neural networks processing systems in recognition and control problems", Neuroinformatics and Neurocomputers; IEEE, 1992, p. 820-828.

Jianguo Fu, Naresh K. Sinha, "An iterative learning scheme for motion control of robots using neural networks: A case study", Journal of Intelligent & Robotic Systems, 1993, p. 375-398.

Troccaz, J. Lavallee, S. Hellion, E., "A passive arm with dynamic constraints: a solution to safety problems in medical robotics", Systems Engineering in the Service of Humans, Conference Proceedings, 1993, p. 166-171.

Swarup, M. Gopal, "Comparative study on linearized robot models", Journal of Intelligent & Robotic Systems, 1993, p. 287-300.

H. Azaria, A. Dvir, "Algorithm optimization using a rule-based system. A case study: The Direct Kinematic Solution in robotics", Journal of Intelligent & Robotic Systems, 1993, p. 309-324.

Erick Garcia-Benitez; Stephen Yurkovich; Kevin M. Passino, "Rule-Based Supervisory Control of a Two-Link Flexible Manipulator", Journal of Intelligent and Robotic Systems, 1993, p. 195-213.

K. Periyasamy, V. S. Alagar, T. D. Bui, "A formal framework for design and verification of robotic agents", Journal of Intelligent & Robotic Systems, 1993, p. 173-200.

S. Nicosia, A. Tornambè, P. Valigi, "State estimation in robotic manipulators: Some experimental results", Journal of Intelligent & Robotic Systems 1993, p. 321-351.

Dimitrios M. Emiris, Vassilios D. Tourassis, "Singularity-robust decoupled control of dual-elbow manipulators", Journal of Intelligent & Robotic Systems, 1993, p. 225-243.

M.M. Bayoumi, "Adaptive Control of Robots with Rigid Links: A Status Report", Department of Electrical Engineering, Queen's University, Ontario, Canada (IEEE), 1993, p. 232-236.

Y. Edan, B. A. Engel, G. E. Miles, "Intelligent control system simulation of an agricultural robot", Journal of Intelligent & Robotic Systems, 1993, p. 267-284.

Chun-Yi Su, "Adaptive sliding mode control of nonlinear robotic systems with time-varying parameters", Systems and Control Let-

(56) References Cited

OTHER PUBLICATIONS ters; Department of Mechanical Engineering, University of Victoria, Victoria, B.C. Canada V8W 3P6, 1993, p. 35-41.
Yalou Huang; Guizhang Lu, "Force Analysis and Hybrid Control Scheme for Multiple Robot Manipulators", Artificial Intelligence and Robotics Research Laboratories; Dept of Computer and System Sciences; Nankai University, China (Proceedings of the 1993 IEEE/RSJ International Conference on Intelligent Robots and Systems in Japan), 1993, p. 1530-1534.
C.M. Lim; T. Hiyama, "Experimental implementation of a fuzzy logic control scheme for a servomotor", Mechatronics; Department of Electronic Engineering, Ngee Ann Polytechnic, Singapore 2159 Singapore.
E. Al-Gallaf, A.J. Allen, K. Warwick, "Dextrous hands: Issues relating to a four-finger articulated hand", Mechatronics; Department of Cybernetics, School of Engineering and Information Sciences, University of Reading, Reading, Berks RG6 2AY, U.K., 1993, p. 329-342.
A. Swarup, M. Gopal, "On robustness of decentralized control for robot manipulators", Robotics and Autonomous Systems; Department of Electrical Engineering, Indian Institute of Technology, New Delhi—110016, India, 1993, p. 109-112.
L. Behera, M. Gopal, Santanu Chaudhury, "Trajectory tracking of robot manipulator using Gaussian networks", Dept. of Electrical Engineering, Indian Institute of Technology, Delhi, Hauz Khas, New Delhi 110 016, India, 1993.
E. V. Panteley, A. A. Stotsky, "Adaptive trajectory/force control scheme for constrained robot manipulators", International Journal of Adaptive Control and Signal Processing, 1993, p. 489-496.
Filaretov, V.F., "A Synthesis of Adaptive Control Systems for Industrial Robots", Electronic Mfg Technology Symposium, 1993, p. 168-171.
S. Zenkevich, A. Maximov, A. Nazarova, A. Korshunov, "Control of robot-based assembly cell", Lecture Notes in Control and Information Sciences , 1993, p. 418-427.
D.E. Whitney, "The Mathematics of Coordinated Control of Prosthetic Arms and Manipulators", Asme Publication, 1972.
Shapiro, "Digital Technology Enables Robots to See", Computer Design, 1978.
Bejczy, A. K., Salisbury, Jr., J. K., "Kinesthetic Coupling Between Operator and Remote Manipulator", Advances in Computer Technology, 1980.
"An Improved CT-Aided Stereotactic Neurosurgery Technique", Fifth Annual Symposium on Computer Applications in Medical Care, 1981, p. 591-595.
Michael L. Thodes, Ph.D, "Stereotactic Neurosurgery Using 3D Image Data From Computed Tomography", Journal of Medical Systems, 1982, p. 106-118.
Salisburg, Jr., J. Kenneth, "Kinematic and Force Analysis of Articulated Hands", 1982.
"Minicomputer Control Robot's Six Electrohydraulic Servoactuators", Hydraulics & Pneumatics, 1982, p. 53-58.
F.M. Kulakov, "Modeling Robot Control in Assembly Operations", Modern Robot Engineering, Moscow, MIR Publishers, 1982, p. 100-116.
Bejczy et al., "Controlling Remote Manipulators Through Kinesthetic Coupling", Computers in Mechanical Engineering, 1983, p. 48-60.
L.E. Weiss, "Dynamic Visual Servo Control of Robots: an adaptive image-based approach, Technical Report", Part 1 Carnegie Mellon, 1984.
Dennis E. Bullard, "CT-Guided Stereotactic Biopsies Using a Modified Grame and Gildenberg Techniques", Journal of Neurology, Neurosurgery and Psychiatry, 1984, p. 590-595.
M. Caporali et al., "Design and Construction of a Five Fingered Robotic Hand", Robotics Age, 1984, p. 14-20.
Salisbury, Jr., J. K., "Design and Control of an Articulated Hand", International Symposium on Dessign and Synthesis, 1984.
L. Dade Lunsford, M.D., "Stereotactic Exploration of the Brain in the Era of Computed Tomography", Surg. Neurol, 1984, p. 222-230.

Jacobsen, S.C., Iversen, E.K., Knutti, D. F., Johnson, R.T., Biggers, K. B., "Design of the Utah/MIT Dexterous Hand", Conf. on Robotics and Automation, 1986.
S. Hayati, M. Mirmirani, "Improving the Absolute positioning Accuracy of Robot Manipulators", Journal of Robotic Systems, 1986, p. 397-413.
Vertut, J., Coiffet, P., "Teleoperations and Robotics Evolution and Development", Robot Technology, 1986, p. 191-194.
L.E. Weiss; A.C. Sanderson, "Dynamic Sensor-based Control of Robots with Visual Feedback", IEEE Journal of Robotics and Automation, 1987, p. 5.
Townsend, W.T., Salisbury, Jr. J. K., "The Effect of Coulomb Friction and Stiction on Force Control", Conf. on Robotics and Automation, 1987.
P. Rives, F. Chaumette, B. Espiau, "Visual Servoing Based on a Task Function Approach", International Symposium on Experimental Robotics (Canada), 1989.
B.L. Davies, R.D. Hibberd, A. Timoney, J.E.A. Wickham, "A surgeon robot for prostatectomies", Proc. of 2nd Int. Conference on Robotics in Medicine (UK), 1989.
J.T. Feddema, C.S.G. Lee, O.R. Mitchell, "Automatic selection of image features for visual servoing of a robot manipulator", Conf. IEEE Robotics and Automation (USA), 1989, p. 14-19.
J.T. Feddema, O.R. Mitchell, "Vision-Guided Servoing with Feature-Based Trajectory Generation", IEEE Transaction on Robotics and Automation, 1989.
Pierre J. de Smet, Eugene I. Rivin, Yongle Lou, D. Kegg, "Robot Performance as Influenced by Mechanical System", CIRP Annals—Manufacturing Technology, 1990, p. 383-386.
Mills, J.K., "Hybrid actuation of robotic manipulators: an integral manifold control approach", Intelligent Control, IEEE, 1990, p. 817-823.
John T. Feddema, C. S. George Lee, "Adaptive Image Feature Prediction and Control for Visual Tracking with A Hand-eye Coordinated Camera", IEEE Transactions on Systems, man, and Cybernetics, 1990, p. 1172-1183.
Rafiqul I. Noorani, "Microcomputer-based robot arm control", Mathematical and Computer Modelling, 1990, p. 450-455.
Elysseev S., Kuznetzov, N., Lukyanov A., "Control of Robot Vibrations", 1990.
C. Samson, B. Espiau, "Robot Control: The Task Function Approach", Oxford Univ., 1990.
Adams, L, Krybus, W., Meyer-Ebrecht, D., Rueger, R., Gilsbach, J.M., Moesges, R., Schloendorff, G., "Computer Assisted Surgery", IEEE Computer Graphics and Application, 1990, p. 43-51.
B. Espiau, F. Chaumette, P. Rives, "A new approach to visual servoing in robotics", Research Report; IRISA/INRIA (France), 1990.
Korikov, Anatoliim, Syriamkin, Vladimiri, Titov, Vitaliis, "Correlation robot vision systems", 1990, p. 264.
Sadegh N, Hopowitz R, "Stability and robustness analysis of a class of adaptive controller for robotic manipulator", The International Journal of Robotics Research, 1990.
Rocheleau, D.N., Crane, C.D., III, "Development of a graphical interface for robotic operation in a hazardous environment", Systems, Man, and Cybernetics, 1991, p. 1077-1081.
J.C. Latombe, "Robot Motion Planning", The Kluwer International Series in Engineering and Computer Science, Kluwer Academic Publishers, 1991.
Kubota, T., Sato, M., Harashima, F., "Visual Control of Robotic Manipulator Based on Neural Networks", Industrial Electronics, IEEE, 1992, p. 490-496.
Nakamura, H., Shimada, T., Kobayashi, H., "An inspection robot for feeder cables-snake like motion control", Industrial Electronics, Control, Instrumentation, and Automation, 1992, p. 849-852.
P. Kazanzides, J. Zuhars, B. Mittelsstadt, R.H. Taylor, "Force sensing and control for a surgical robot", IEEE conference on Robotics and Automation (Nice), 1992, p. 612-617.
Vsevolod I. Astafyev FARUS, Yakutsk, Russia Yuri M. Gorsky, "Homeostatics", Cybernetics and applied systems, 1992, p. 7-22.
F.M. Kulakov, Russian Research on Robotics, Intelligent Autonomous Systems, 1995, p. 53-62.

(56) References Cited

OTHER PUBLICATIONS

Shevtsova N.A., Faure A., Klepatch A.A., Podladchikova L.N., Rybak I.A., Model of Foveal Visual Preprocessor, Intelligent Robots and Computer Vision XIV: Algorithms, Techniques, Active Vision, and Materials Handling, 1995, p. 588-596.
Reynolds, O., "On Efficiency of Belts or Straps as Communicators of Work", The Engineer, 1874, p. 396.
Swift, H. W., "Power Transmission by Belts: An Investigation of Fundamentals", The Institution of Mechanical Engineers, 1928.
Smith, G. A. et al., "Surgery", 1950, p. 817-821.
"Baby Robot", http://cyberneticzoo.com/wp-content/uploads/2010/03/Ticket-robot-russian-1973.pdf, 1970.
Rajac, "Variable-Pitch Transfer Mechanism", IBM Technical Disclosure Bulletin, 1974.
Zh Luo, "Theoretical and Experimental Study on Control of Flexible Robot Arms Using Direct Strain Feedback", 1992.
Bu Yonghong, Wang Yi, "The Identification of Geometric Link Parameters of Robot Manipulators", ACTA Automatica Sinica, 1992.
Zheng Nanning Wang Long Hu chao Liu Jianqin, "Improved BP Neural Net and Its Application to Handwritten Numeral Recognition", 1992.
Stefano Chiaverini, Bruno Siciliano, Olav Egeland, Robot Control in Singular Configurations—Analysis and Experimental Results, Experimental Robotics II, 1993, p. 25-34.
Antonio Bicchi, J. Kenneth Salisbury, David L. Brock, Experimental Evaluation of Friction Characteristics With an Articulated Robotic Hand, Experimental Robotics II, 1993, p. 153-167.
Claudio Melchiorri, Gabriele Vassura, Mechanical and Control Issues for Integration of an Arm-Hand Robotic System, Experimental Robotics II, 1993, p. 136-152.
Andrew K. Rist, Ellen Y. Lin, Bartholomew O. Nnaji, Ralph Application for Surface Mount Assembly, International Journal of Flexible Manufacturing Systems, 1993, p. 27-52.
R.H. Taylor, et. al, A Model-Based Optimal Planning and Execution System With Active Sensing and Passive Manipulation for Augmentation of Human-Precision in Computer-Integrated Surgery, Lecture Notes in Control and Information Sciences; Experimental Robo.
Nobuyuki Furuya, Masatomo Matubara, An Algorithm of Motor Control by Software Servo System (2nd Report): Application to 4-Axes Scara Robot, Journal of the Japan Society of Precision Engineering, 1993, p. 423-428.
H.S. Moon, S.Y. Lee, S.J. Na, A Study on Selection of Gas Metal Arc Welding Parameters of Fillet Joints Using Neural Network, Journal of the Korean Welding Society, 1993, p. 151-160.
Byong Suk Kim, Computer-Assisted System for Accident Analysis and Mul-Function Protection in Industrial Robot, Papersearch.net (Korean Studies Information Co.), 1993, p. 61-64.
J. I. Arocena, R. W. Daniel, P. Elosegui, End Point Control of Compliant Robots, Experimental Robotics II, 1993, p. 435-449.
Ho Kyung Kim, Nonlinear Static Analysis and Determination of Initial Equilibrium States of Suspension Bridges, 1993, p. 177-186.
Gimdongha, imhyeongyo (Dong Ha Kim, Hyeon Kyo Lim), Safe Speed Limit of Robot Arm During Teaching and Maintenance Work, 1993, p. 64-70.
Chang-Boo Kim, Seung-Hoon Lee, Inverse Dynamic Analysis of a Flexible Robot Arm With Multiple Joints by Using the Optimal Control Method, Journal of the Korean Society of Precision Engineering, 1993, p. 133-140.
Chang-Soo Han, The Optimum Design of a 6 D.O.F. Fully-Parallel Micromanipulator for Enhanced Robot Accuracy, Journal of the Korean Society of Precision Engineering, 1993, p. 42-51.
Nicholas Jackson, The Story Behind the Russian Robot Collie Patent Sketches, The Atlantic, 2011.
Oh Joong Chan, Jong Sik Boong, Choi Ko Bong, Kwon Key Jo, Design a Mobile Robot's Tracking Control System Using Fuzzy Theory, Sung Kyun Kwan Univ., 1992, p. 112-115.
Sang-Gwon Lim, Jin-Won Lee, Yong-Ky Moon, Dong-Lyeol Jeon, Sang-Hyun Jin, In-Hwan Oh, Dong-Il Kim, Sung-Kwun Kim, Development of AC Servo Motor Controller for Industrial Robotand CNC Machine System, Control R/D Team, Samsung Electronics, 1992, p. 1211-1214.
E.S. Jeon, S.H. Park, J.E. Oh, Singylarty Control of Robot Wrist Joints Using Euler Parameters, Journal of the Korean Society of Precision Engineering, 1992, p. 11-152.
Yoon Seok Chang, Hakil Kim, Motion Estimation of Moving Objects Using Frequency Domain Transforms, 1992, p. 92-99.
Nam Gu Lee, Chong Soo Lee, Chong Kug Park, Dynamic Hybrid Position/Force Controller for Two Cooperating Robots, 1992, p. 103-107.
Jong-Wu Moon, Jeung Park, Chong-Xuk Park, Adaptibe Control of a Flexible Robot Manipulator—Using ARMA Prediction Model, 1992, p. 122-127.
Dae-Gab Gweon, Choong-Min Jung, Development of a Robot Wrist for the Assembly of Chamferless Parts, Journal of the Korean Society of Precision Engineering, 1992, p. 36-43.
Fumio Harashima, Yaskuhiko Dote, Sensor-Based Robot Systems, Proc. IEEE Int. Symposium; Muroran Institute of Tech. (Japan), 1992, p. 10-19.
Chang-Boo Kim, Seung-Hoon Lee, Formulation of the Equation of Motion for Flexible Robotics Arms by Using the Finite Element Method, Inha Univ., Daewoo Heavy Industries LTD, 1992, p. 233-238.
Jin-Geol Kim, A Study on the Robust Digital Tracking Control of a Robot With Flexible Joints, Journal of the Korean Society of Precision Engineering, 1992, p. 92-100.
Han-Sig Lee, The Prospects for the Future on Research of Flexible Automation and Robot System, 1992, p. 37-38.
Young Hood Joo, Seok Joo Yi, San Yeob Cha, Kwang Bang Woo, Hyung Woo Yoon, Gun Woong Hae, Sung Kwun Kim, A Study on Optimal Navigation of Autonomous Mobile Robot, Production of Eng. Division, Samsung Electronics Co., 1992, p. 128-133.
H. C. Shen, W. P. Yan, G. E. Taylor, Intelligent Sensory Decision-Making for Error Identification in Autonomous Robotics Systems, The International Journal of Advanced Manufacturing Technology, 1993, p. 377-384.
Morris R. Driels, W. Swayze, S. Potter, Full-Pose Calibration of a Root Manipulator Using a Coordinate-Measuring Machine, The International Journal of Advanced Manufacturing Technology, 1993, p. 34-41.
M. Wu, B. C. Jiang, Y. R. Shiau, Controlling a Robot'S Position Using Neural Networks, The International Journal of Advanced Manufacturing Technology, 1993, p. 216-226.
Joachim O. Berg, Path and Orientation Accuracy of Industrial Robots, The International Journal of Advanced Manufacturing Technology, 1993, p. 29-33.
Shaheen Ahmad, Mohamed Zribi, Lyapunov-Based Control Design for Multiple Robots Handling a Common Object, Dynamics and Control, 1993, p. 127-157.
S.D. Park, K.W. Jeong, W.K. Chung, Y. Youm, Development of a Control Method Using Both Electric and Pneumatic Actuators for a Heavy Load Handing Robot, Journal of the Korean Society of Precision Engineering, 1993, p. 14-21.
Nicolay V. Kim, Algorithms of Observation Information Synthesis, International Conference on Electronics, Informations and Communications, 1993, p. 120-124.
Sung Do Chi, Seok Pil Lee, Wang Jae Lee, San Hui Park, Hierarchical Design of Intelligent Robot System, Hankuk Aviation Univ., Yonsel Univ., 1993, p. 213-216.
Cai Zi-Xing, Jiang Zhiming, High-Level Expert System-Based Robot Planning, 1993.
Yong-Deuk Seo, Dong-Joon Choi, Ki-Sang Hong, Hong Joeng, The Development of Intelligent Robot Using Vision and Speech Recognition System, Department of EE, Postech, 1993, p. 39-44.
Jae-Hun Jung, Yong-Hyun Jung, Jong-Mo Kim, Suck-Gyu Lee, Dal-Hae Lee, Motion Control of Autonomous Mobile Robot With Fuzzy Algorithm, Yeungnam Univ., 1993, p. 362-365.
Jin-Seob Choi, Dong-Won Kim, Sung-Mo Yang, A Study on the Pseudoinverse Kinematic Motion Control of 6-Axis Arc Welding Robot, Journal of the Korean Society of Precision Engineering, 1993, p. 170-177.

(56) References Cited

OTHER PUBLICATIONS

A Study on a Basic System Configuration for the PC Interface and the Robot Trajectory Generation, 1993, p. 354-358.
G.T. Yang, S.D. Ahn, S.C. Lee, Tip Position Control of Flexible Robot Arm by Self-Tuning Fuzzy Algorithm, Chonbuk Univ., 1993, p. 213-217.
Jeong Park, Hoe-Young Yoo, The Study of the Method of Position Control for the One-Link Flexible Robot Arm, 1993, p. 57-60.
ASEA Industrial Robot System IRb-60, 1975, p. 1-8.
Robots Take a Hold on Production, 1982, p. 122-129.
M. Peter Heilburn, M.D., J., Preliminary Experience With Brown-Robert-Wells (BRW) Computerized Tomography Stereotaxis Guidance System, Neurourgery, 1983, p. 217-221.
International Machine Intelligence Robot System Users Manual, International Machine Intelligence, 1983.
Orbitran Wafer Handling Robot, Genmark Automation, 1989, p. 2,3,4.
H Kojima, R Toyama, Development of Wall Cleaning Robot, 1992.
International Search Report and Written Opinion dated Nov. 28, 2012, issued in related International Application No. PCT/US2012/040414.
International Search Report and Written Opinion dated Feb. 27, 2013, issued in related International Application No. PCT/US2012/054802.
International Search Report and Written Opinion dated Apr. 25, 2013, issued in related International Application No. PCT/US2012/070924.
International Search Report and Written Opinion dated Apr. 6, 2012 issued in related International Application No. PCT/US2011/044811.
International Search Report and Written Opinion dated May 31, 2012, issued in related International Application No. PCT/US2011/060214.
Australia Office Action dated Jun. 19, 2014, issued in related Australia Application No. 2011283048.
International Search Report and Written Opinion dated Dec. 9, 2013, issued in related International Application No. PCT/US2013/054326.
International Search Report and Written Opinion dated May 30, 2012, issued in related International Application No. PCT/US2011/057282.
Extended European Search Report dated Sep. 16, 2014 issued in European Application No. 12793169.9-1660 / 2713931.
Notice of Allowance and English translation issued in related Japanese Application 2013-535114 dated Jan. 30, 2015.
L.E. Weiss, "Dynamic Visual Servo Control of Robots: an adaptive image-based approach, Technical Report", Part 2 Carnegie Mellon, 1984.
L.E. Weiss, "Dynamic Visual Servo Control of Robots: an adaptive image-based approach, Technical Report", Part 3 Carnegie Mellon, 1984.
"Highly articulated Robotic Probes and Methods of Production and Use of Such Probes" Specification, Drawings, Claims, and Prosecution History of U.S. Appl. No. 13/880,525, filed Dec. 31, 2014, by Joseph A. Stand.
Antonio Bicchi, J. Kenneth Salisbury, David L. Brock, Experimental Evaluation of Friction Characteristics With an Articulated Robotic Hand, Experimental Robotics II, 1993, 153-167.
Andrew K. Rlst, Ellen Y. Lin, Bartholomew O. Nnaji, Ralph Application for Surface Mount Assembly, International Journal of Flexible Manufacturing Systems, 1993, p. 27-52.
Dae-Gab Gweon, Choong-Min Jung, Development of a Robot Wrist for the Assembly of Chamferless Parts, Journal of the Korean Society of Precision Engineering , 1992, 36-43.
Xu Hongbin, "Stability and performance robustness analysis of hybrid control for robot manlpulators", Journal of UEST of China, vol. 22 No. 5, Oct. 1993, p. 501-505.
"Highly Articulated Robotic Probes and Methods of Production and Use of Such Probes" Specification, Drawings and Prosecution History, of U.S. Appl. No. 13/880,525, filed Sep. 17, 2013, by Joseph A. Stand, et al.
Potemkin, E., Astafurov, P., Osipov, A., Malenkov, M., Mishkinyuk, V., Sologub, P., "Remote-controlled robots for repair and recovery in the zones of high radiation levels", Robotics and Automation, IEEE, 1992, 80-82.
Fllaretov, V.F., "A Synthesis of Adaptive Control Systems for Industrial Robots", Electronic Mfg Technology Symposium, 1993, p. 168-171.
L.E. Weiss, "Dynamic Visual Servo Control of Robots: an adaptive image-based approach, Technical Report", Carnegie Mellon, 1984.
H.A. Paul, B. Mittelstadt, W.L. Barger, B. Musits, R.H. Taylor, P. Kazanzides, J. Zuhars, B. Williamson, W. Hanson, "A surgical robot for total hip replacement surgery", IEEE Conference on Robotics and Automation (Nice), 1992, p. 606-611.
Giullo E. Lancioni, Domenico Bellini, Doretta Oliva, "A robot to provide multi-handicapped blind persons with physical guidance and activity choices", Journal of Developmental and Physical Disabilities, 1993, p. 337-348.
Summary of OA and comments for Japanese Patent Application No. 2013-538895 based on International Appliation No. PCT/US2011/060214.
Partial European Search Report dated Apr. 11, 2016 in corresponding European Application No. 11835214.5.
Extended European Search Report dated Aug. 17, 2016 issued in corresponding European Application No. 11 83 5214.
Canadian Office Action dated Apr. 21, 2017 issued in corresponding Canadian Application No. 2815396.
Australian Office Action dated Jan. 12, 2018, issued in corresponding Australian Application No. 2016208441.
European Office Action dated Sep. 19, 2017 issued in corresponding European Application No. 1835214.5.
Canadian Office Action dated Mar. 21, 2018 issued in corresponding Canadian Application No. 2815396.
S. Lavallee, J. Troccaz, L. Gaborit, A.L. Benabid, D. Hoffman, "Image guided operating robot: A clinical application in stereotactic neurosurgery", IEEE Conference on Robotics and Automation (Nice), 1992.
H.A. Paul, B. Mittelstadt, W.L. Bargar, B. Musits, R.H. Taylor, P. Kazanzides, J. Zuhars, B. Williamson, W. Hanson, "A surgical robot for total hip replacement surgery", IEEE Conference on Robotics and Automation (Nice), 1992, p. 606-611.
R.H. Taylor, et. al, Augmentation of Human Precision in Computer-Integrated Surgery, Innov. Tech. Biol. Med., 1992.
Takashi Matsui, Mochizuki Yoshihiro, Effect of Positive Angular Velocity Feedback on Torque Control of Hydraulic Actuator, JSME international journal, 1992, p. 406-412.
Ph, Cinquin, et. al, IGOR: Image Guided Operating Robot. Methodology, Medical Applications, Results, Innov. Tech. Biol. Med., 1992, p. 1048-1049.
Heung-Joo Jeon, Bum-Hee Lee, Robot Motion Planning for Time-Varying Obstacle Avoidance Using the Distance Function, 1992, p. 1429-1438.
Bose, B., Kalra, A.K., Thukral, S., Sood, A., Guha, S.K., Anand, S., Tremor Compensation for Robotics Assisted Microsurgery, Engineering in Medicine and Biology Society, 1992, p. 1067-1068.
Kenneth L. Hillsley, Stephen Yurkovich, Vibration Control of a Two-Link Flexible Robot Arm, Dynamics and Control, 1993, p. 261-280.
Canudas de Wit, C., Ortega, R., Seleme, S.I., Robot Motion Control Using Induction Motor Drives, Robotics and Automation, 1993, p. 533-538.
Rovetta A., Wen X. (1993) Telemanipulation control of a robotic hand with cooperatingfingers by means of telepresence with a hybrid virtual-real structure. In: Morecki A., Bianchi G., Jaworek K. (eds) RoManSy 9. Lecture Notes in Control and Information Sciences, vol. 187. Springer, Berlin, Heidelberg.
James K. Mills, Hybrid Actuator for Robot Manipulators: Design, Control and Performance, Robotics and Automation, IEEE Conference, 1993, p. 19-38.

(56) References Cited

OTHER PUBLICATIONS

Pietro Fanghella, Carlo Galletti, An Approach to Symbolic Kinematics of Multiloop Robot Mechanisms, RoManSy9, 1993, p. 33-40.
Yozo Fujino, Pennung Warnitchai, B.M. Pacheco, Active Stiffness Control of Cable Vibration, Journal of Applied Mechanics, 1993, p. 948-953.
Ng, W.S. Davies, B.L. Hibberd, R.D. Timoney, A.G., Robotic Surgery, Engineering in Medicine and Biology Magazine, 1993, p. 120-125.
J.L. Dallaway, R.M. Mahoney, R.D. Jackson, R.G. Gosine, An Interactive Robot Control Environment for Rehabilitation Applications, Robotica, 1993, p. 541-551.
Giulio E. Lancioni, Domenico Bellini, Doretta Oliva, "A robot to provide multi-handicapped blind persons with physical guidance and activity choices", Journal of Developmental and Physical Disabilities, 1993, p. 337-348.
Melzer A, Schurr MO, Kunert W, Buess G, Voges U, Meyer JU., Intelligent Surgical Instrument System ISIS. Concept and Preliminary Experimental Application of Components and Prototypes, Endosc Surg Allied Technol., 1993, p. 165-170.
John G. Hunter, Jonathan M. Sackier, Minimally Invasive Surgery, McGraw Hill, Inc., Health Professions Division, 1993.
Zhao Yu-shan Gu Liang-xian , Generalized Dynamic Model for Multibodies Manipulator, 1993.

* cited by examiner

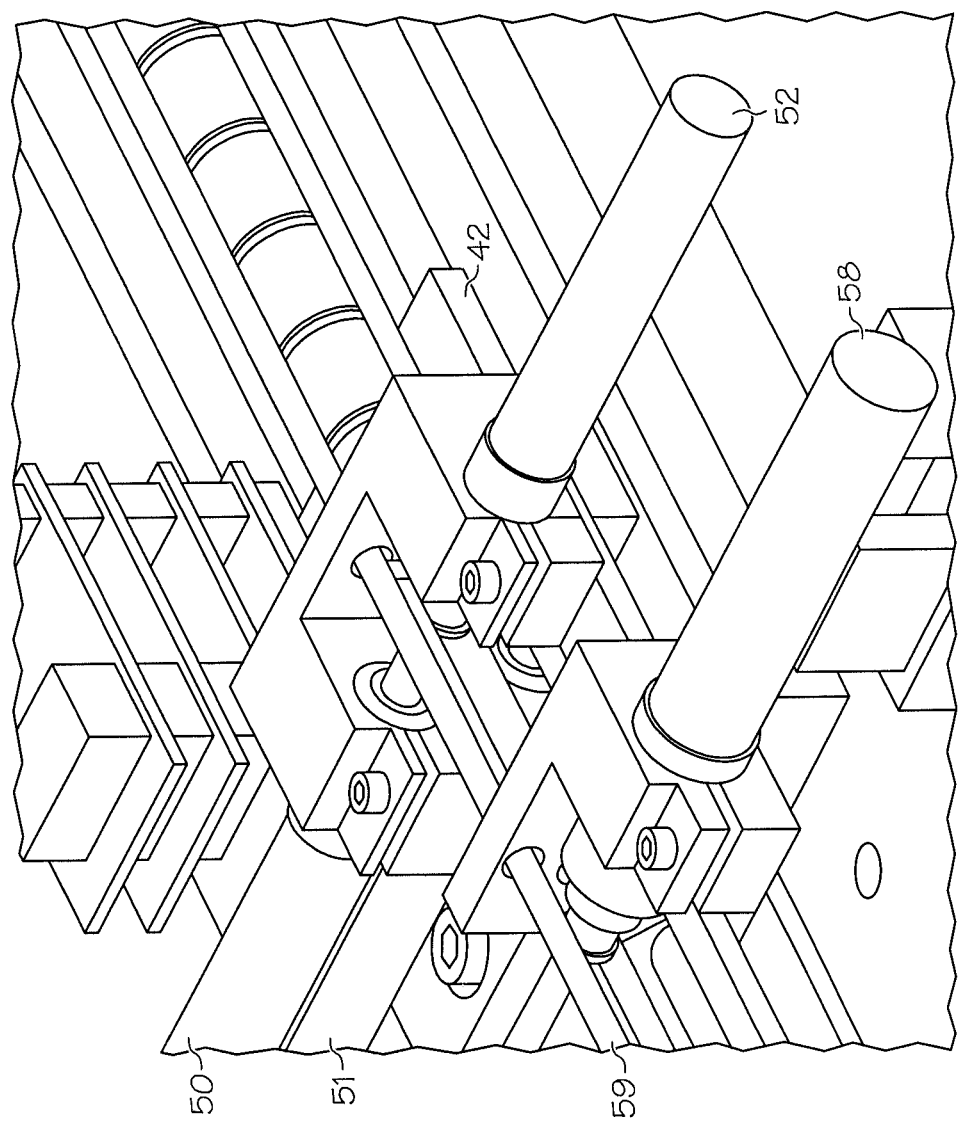

HIGHLY ARTICULATED ROBOTIC PROBES AND METHODS OF PRODUCTION AND USE OF SUCH PROBES

RELATED APPLICATIONS

This application is a continuation application of U.S. patent application Ser. No. 13/880,525, filed on Apr. 19, 2013, which claims the benefit of United States PCT application serial number PCT/US2011/057282, filed on Oct. 21, 2011, which claims the benefit of U.S. Provisional Application No. 61/406,032, filed Oct. 22, 2010, the content of which is incorporated herein by reference in its entirety.

United States PCT application serial number PCT/US2011/057282, filed on Oct. 21, 2011 also claims the benefit of U.S. Provisional Application No. 61/534,032, filed Sep. 13, 2011, the content of which is incorporated herein by reference in its entirety.

United States PCT application serial number PCT/US2011/057282, filed on Oct. 21, 2011 also claims the benefit of U.S. Provisional Application No. 61/412,733, filed Nov. 11, 2010, the content of which is incorporated herein by reference in its entirety.

United States PCT application serial number PCT/US2011/057282, filed on Oct. 21, 2011 also claims the benefit of U.S. Provisional Application No. 61/472,344, filed Apr. 6, 2011, the content of which is incorporated herein by reference in its entirety.

United States PCT application serial number PCT/US2011/057282, filed on Oct. 21, 2011 also claims the benefit of U.S. Provisional Application No. 61/492,578, filed Jun. 2, 2011, the content of which is incorporated herein by reference in its entirety.

This application is related to U.S. Provisional Application No. 61/368,257, filed Jul. 28, 2010, the content of which is incorporated herein by reference in its entirety.

This application is related to PCT Application No PCT/US2011/044811, filed Jul. 21, 2011, the content of which is incorporated herein by reference in its entirety.

This application is related to U.S. patent application Ser. No. 11/630,279, filed Dec. 20, 2006, published as U.S. Patent Application Publication No. 2009/0171151, the content of which is incorporated herein by reference in its entirety.

FIELD

Embodiments relate generally to the field of robotics and, more particularly, to three dimensional, flexible, steerable robotic devices.

BACKGROUND

There are numerous types of steerable multi-linked probes, and such devices are utilized in a variety of different applications. Robert Sturges' U.S. Pat. No. 5,759,151, which is hereby incorporated by reference in its entirety, discloses a flexible, steerable device for conducting exploratory procedures. The device includes at least one spine, each having stiffening means for selectively rendering the spine rigid and flexible along its length. A flexible sheath surrounds the spine and is axially slidably moveable relative to the spine so that the sheath will follow and conform to the shape of a spine in the rigid state and resist further flexure when the spine is in a relaxed state. A steerable distal tip is provided on the distal end of the device. Controls for the distal tip are mounted on the proximal end of the device. Mechanisms are provided on the distal end of the device for selectively activating and deactivating the stiffening means of the spine. An instrument conduit may be mounted on the sheath. Howard Choset's U.S. patent application Ser. No. 11/630,279, which is hereby incorporated by reference in its entirety, discloses a feeder mechanism for advancing and retracting both an inner core and an outer sleeve, as well as selectively applying tension to control cables used for steering and causing either the inner core or outer sleeve to transition between a rigid state and a limp state.

U.S. Pat. No. 6,610,007, incorporated herein by reference, discloses a steerable endoscope having an elongated body with a selectively steerable distal portion and an automatically controlled proximal portion. The endoscope body is inserted into a patient and the selectively steerable distal portion is used to select a desired path within the patient's body. When the endoscope body is advanced, an electronic motion controller operates the automatically controlled proximal portion to assume the selected curve of the selectively steerable distal portion. Another desired path is selected with the selectively steerable distal portion and the endoscope body is advanced again. As the endoscope body is further advanced, the selected curves propagate proximally along the endoscope body, and when the endoscope body is withdrawn proximally, the selected curves propagate distally along the endoscope body. This creates a serpentine motion in the endoscope body allowing it to negotiate tortuous curves along a desired path through or around and between organs within the body.

For medical use and other critical applications, it is extremely important that each device not only perform as intended and within known specifications, but have repeatable performance and otherwise consistent operation from use to use. For these and other reasons, there is a need for improved systems, devices, and methods.

SUMMARY

According to one embodiment, an articulated probe having at least a portion configured to be controllably rigid and flexible, includes an inner core having a plurality of inner links; an inner cable extending through the plurality of inner links and configured to control the inner core; an outer sleeve having a plurality of outer links; and a plurality of outer cables extending through the plurality of outer links and configured to control the outer sleeve, wherein the inner cable has a tensile strength greater than each of the individual outer cables.

In some embodiments, the tensile strength of the inner cable is approximately equal to a combined tensile strength of the plurality of outer cables.

In some embodiments, each of the plurality of outer cables has approximately the same tensile strength.

In some embodiments, the tensile strength of each of the plurality of outer cables is approximately 1/Nth of a tensile strength of the inner cable, where N is the number of outer cables.

In some embodiments, each of the plurality of outer cables has approximately the same cross-sectional area.

In some embodiments, the cross-sectional area of each of the plurality of outer cables is approximately 1/Nth of a cross-sectional area of the inner cable, where N is the number of outer cables.

In some embodiments, the inner cable and the plurality of outer cables are comprised of at least one of steel, polyethylene, nylon and fluorocarbons.

According to another embodiment, an articulated probe includes a plurality of links configured to pivot relative to one another through a maximum pivot angle; and an elongated member, wherein at least two of the plurality of links includes a channel for receiving the elongated member therein, and wherein the channel in each of the plurality of links is tapered in an amount sufficient to permit the plurality of links to pivot through the maximum pivot angle while providing a substantially continuous surface between the channels of the links for the elongated member.

In some embodiments, the articulated probe comprises an inner core comprising a plurality of inner links, and wherein the channel is positioned within at least two of the plurality of inner links.

In some embodiments, the articulated probe comprises an outer sleeve comprising a plurality of outer links, and wherein the channel is positioned within at least two of the plurality of outer links.

In some embodiments, the articulated probe comprises an outer sleeve comprising a plurality of outer links; an inner core comprising a plurality of inner links; wherein the channel is positioned between at least two of the plurality of outer links and at least two of the plurality of inner links.

In some embodiments, the at least two of the plurality of links comprises a side port and the channel is positioned within the side port.

In some embodiments, the channel comprises a recess in the at least two of the plurality of links.

In some embodiments, the taper is approximately twice the maximum pivot angle.

In some embodiments, the taper is approximately 26 degrees and the maximum pivot angle is approximately 13 degrees.

In some embodiments, a diameter of the elongated member is less than a diameter of the channels of the links.

In some embodiments, the elongated member includes at least one of a tool and a cable.

In some embodiments, the elongated member includes an inner core formed of a plurality of inner links.

According to yet another embodiment, an articulated probe with a probe central axis includes an inner core having a plurality of inner links configured to pivot relative to one another and the probe central axis through an inner maximum pivot angle; and an outer sleeve having a plurality of outer links configured to pivot relative to one another and the probe central axis through an outer maximum pivot angle, and wherein the inner maximum pivot angle is no less than the outer maximum pivot angle.

In some embodiments, the plurality of outer links in the outer sleeve includes: a first outer link with a first central axis that can align with the probe central axis, the first outer link including an outwardly extending first flange with a first engagement surface extending radically outward relative to the first central axis; and a second outer link with a second central axis that can align with the probe central axis, the second outer link including an outwardly extending second flange with a second engagement surface extending radically outward relative to the second central axis, wherein the first outer link and second outer link are configured to permit the first and second outer links to pivot relative to one another and the probe central axis through the outer maximum pivot angle until the first engagement surface engages the second engagement surface.

In some embodiments, the first engagement surface tapers relative to a line perpendicular to the first central axis.

In some embodiments, the second engagement surface tapers relative to a line perpendicular to the second central axis.

In some embodiments, the first engagement surface tapers approximately 6.5° degrees and the second engagement surface tapers approximately 6.5° degrees.

In some embodiments, the outer maximum pivot angle is no greater than approximately 13 degrees.

In some embodiments, at least one of the plurality of inner links and the plurality of outer links includes channels configured to receive an elongated member therein, wherein the channels are tapered in an amount sufficient to permit pivoting through the outer maximum pivot angle while providing a substantially continuous surface between the channels for the elongated member.

According to another embodiment, an articulated probe, includes a plurality of links configured to pivot relative to one another, wherein the plurality of links includes a first link having a first concave portion and a first convex portion; a second link have a second concave portion and second convex portion, wherein the first convex portion of the first link pivotally engages the second concave portion of the second link, and wherein the first convex portion has a radius of curvature no greater than a radius of curvature of the second concave portion.

In some embodiments, each of the plurality of links has a concave portion and a convex portion that engage corresponding convex and concave portions of adjacent links, and the convex portions each have a radius of curvature no greater than a radius of curvature of the corresponding concave portion.

In another embodiment, a method of performing a surgical procedure comprises: selecting the articulated probe as described in any of the embodiments herein; and manipulating the probe to position at least one tool.

In another embodiment, a method of producing a link for an articulated probe formed of a plurality of links includes the steps of molding the link in molding device, including forming at least one engagement surface configured to engage an adjacent link in the articulated probe; ejecting the link from the molding device by pressing at least one ejection pin against an ejection surface of the link that will not engage an adjacent link in the articulated probe.

In some embodiments, the ejection surface is located in a recess in the link.

In another aspect, embodiments are directed to an articulated probe as described in reference to the figures.

In another aspect, embodiments are directed to a method of performing a medical procedure as described in reference to the figures.

BRIEF DESCRIPTION OF THE DRAWINGS

The foregoing and other objects, features and advantages of embodiments of the present inventive concepts will be apparent from the more particular description of embodiments, as illustrated in the accompanying drawings in which like reference characters refer to the same elements throughout the different views. The drawings are not necessarily to scale, emphasis instead being placed upon illustrating the principles of the embodiments.

FIG. 6 illustrates devices for controlling the tension on cables, in accordance with the present inventive concepts;

DETAILED DESCRIPTION OF EMBODIMENTS

Embodiments of the present inventive concepts will now be described more fully hereinafter with reference to the accompanying drawings. This inventive concepts may, however, be embodied in different forms and should not be construed as limited to the embodiments set forth herein. Like numbers refer to like elements throughout the specification.

It will be understood that, although the terms first, second, third etc. may be used herein to describe various limitations, elements, components, regions, layers and/or sections, these limitations, elements, components, regions, layers and/or sections should not be limited by these terms. These terms are only used to distinguish one limitation, element, component, region, layer or section from another limitation, element, component, region, layer or section. Thus, a first limitation, element, component, region, layer or section discussed below could be termed a second limitation, element, component, region, layer or section, and vice-versa, without departing from the teachings of the present application.

It will be understood that when an element is referred to as being "on" or "connected" or "coupled" to another element, it can be directly on or connected or coupled to the other element or intervening elements can be present. In contrast, when an element is referred to as being "directly on" or "directly connected" or "directly coupled" to another element, there are no intervening elements present. Other words used to describe the relationship between elements should be interpreted in a like fashion (e.g., "between" versus "directly between," "adjacent" versus "directly adjacent," etc.). When an element is referred to herein as being "over" another element, it can be over or under the other element, and either directly coupled to the other element, or intervening elements may be present, or the elements may be spaced apart by a void or gap.

The terminology used herein is for the purpose of describing particular embodiments and is not intended to be limiting of the invention. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements, and/or components, but do not preclude the presence or addition of one or more other features, integers, steps, operations, elements, components, and/or groups thereof.

Overview of Highly Articulated Robotic Probe

Figure 1A:
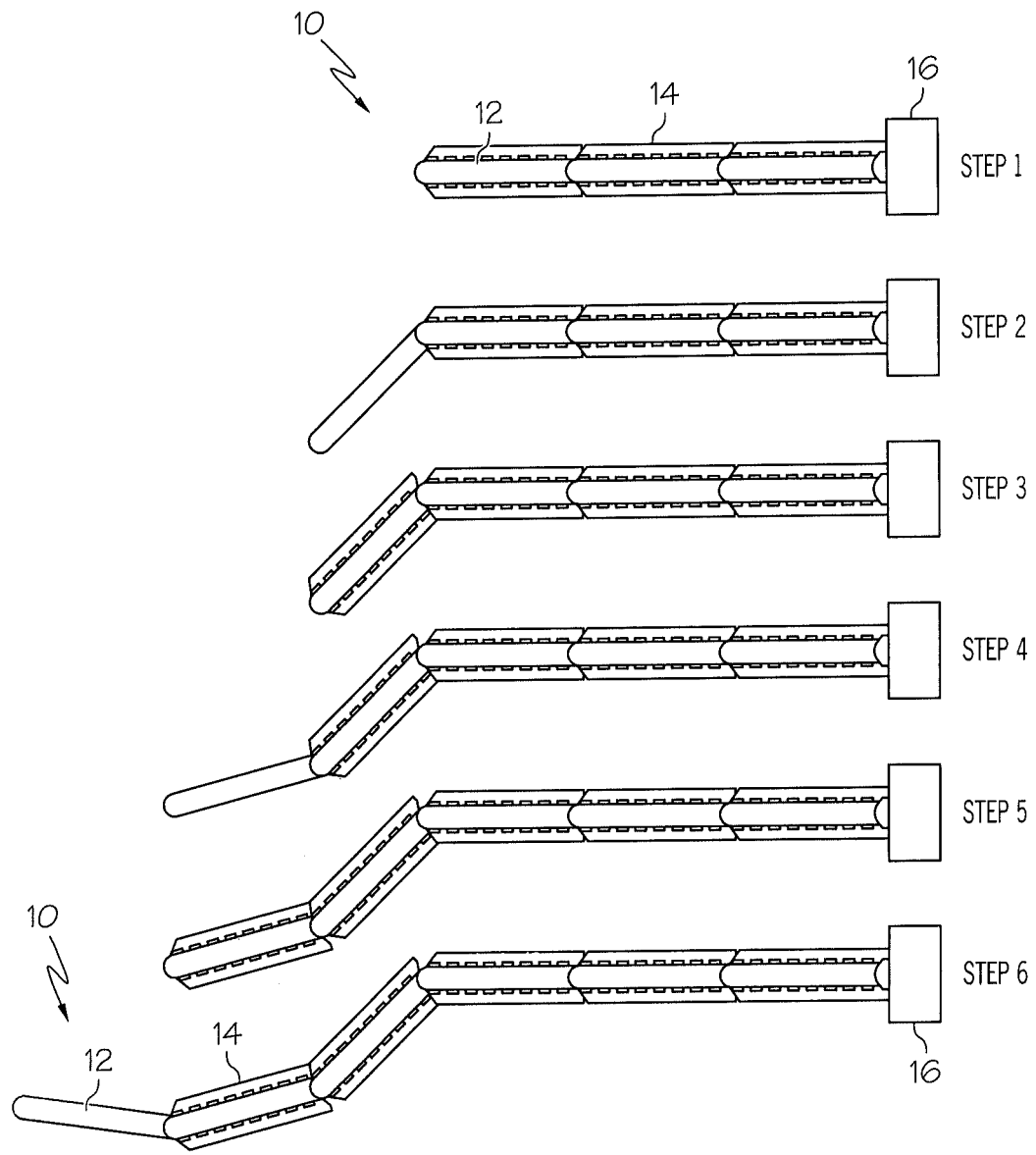
FIGS. 1A-1C are graphic demonstrations of a highly articulated probe device, in accordance with the present inventive concepts.
Figure 1B:
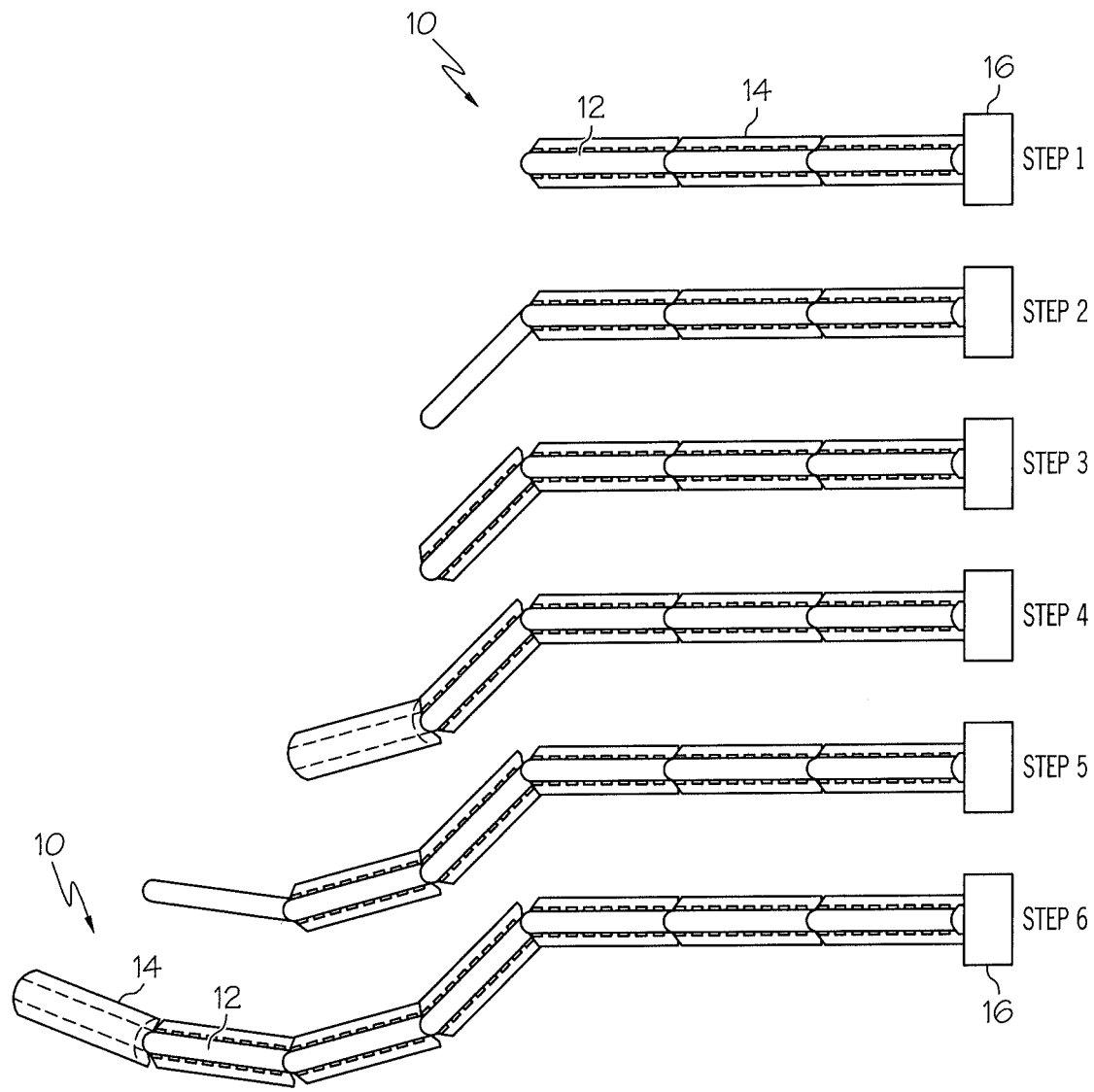
Figure 1C:
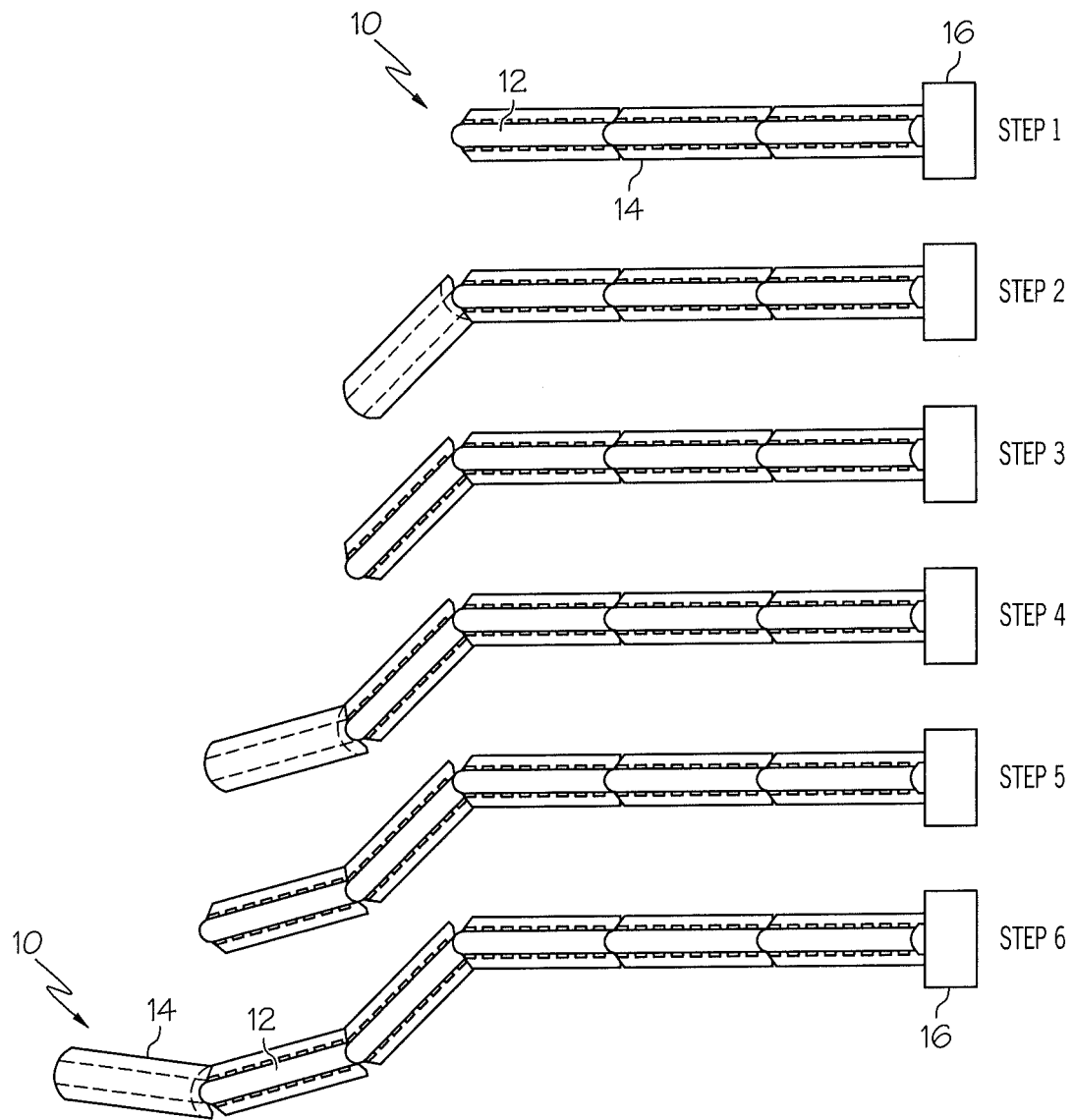

A highly articulated robotic probe 10, according to one embodiment shown in FIGS. 1A-1C, is essentially two concentric mechanisms, an outer one and an inner one, each of which can be viewed as a steerable mechanism. FIGS. 1A-1C show the concept of how different embodiments of the probe 10 operate. Referring to FIG. 1A, the inner mechanism is referred to as a first mechanism, an inner core or inner core mechanism 12. The outer mechanism is referred to as a second mechanism, an outer sleeve or outer sleeve mechanism 14. Each mechanism can alternate between being rigid and limp. In the rigid mode or state, the mechanism is just that—rigid. In the limp mode or state, the mechanism is highly flexible and thus either assumes the shape of its surroundings or can be reshaped. It should be noted that the term "limp" as used herein does not denote a structure that passively assumes a particular configuration dependent upon gravity and the shape of its environment; rather, the "limp" structures described in this application are capable of assuming positions and configurations that are desired by the operator of the device, and therefore are articulated and controlled rather than flaccid and passive.

With this probe 10, one mechanism starts limp and the other starts rigid. For the sake of explanation, assume the outer sleeve 14 is rigid and the inner core 12 is limp, as seen in step 1 in FIG. 1A. Now, the inner core 12 is both pushed forward by a feeding mechanism 16, described below, and its "head" or distal end is steered, as seen in step 2 in FIG. 1A. Now, the inner core 12 is made rigid and the outer sleeve 14 is made limp. The outer sleeve 14 is then pushed forward until it catches up or is coextensive with the inner core 12, as seen in step 3 in FIG. 1A. Now, the outer sleeve 14 is made rigid, the inner core 12 limp, and the procedure then repeats. One variation of this approach is to have the outer sleeve 14 be steerable as well. The operation of such a device is illustrated in FIG. 1B. In FIG. 1B it is seen that each mechanism is capable of catching up to the other and then advancing one link beyond. According to one embodiment, the outer sleeve 14 is steerable and the inner core 12 is not. The operation of such a device is shown in FIG. 1C.

In medical applications, once the probe 10 arrives at a desired location, the operator, typically a surgeon, can slide one or more tools through one or more channels of outer sleeve 14, inner core 12, or a channel formed between outer sleeve 14 and inner core 12, such as to perform various diagnostic and/or therapeutic procedures. In addition to clinical procedures such as surgery, probe 10 can be used in numerous applications including but not limited to: engine inspection, repair or retrofitting; tank inspection and repair; spying and surveillance applications; bomb disarming; inspection or repair in tightly confined spaces such as submarine compartments or nuclear weapons; structural inspections such as building inspections; hazardous waste remediation; biological sample recovery such as anthrax recovery; and combination of these. Clearly, the device of the present disclosure has a wide variety of applications and should not be taken as being limited to any particular application.

Figure 2A:
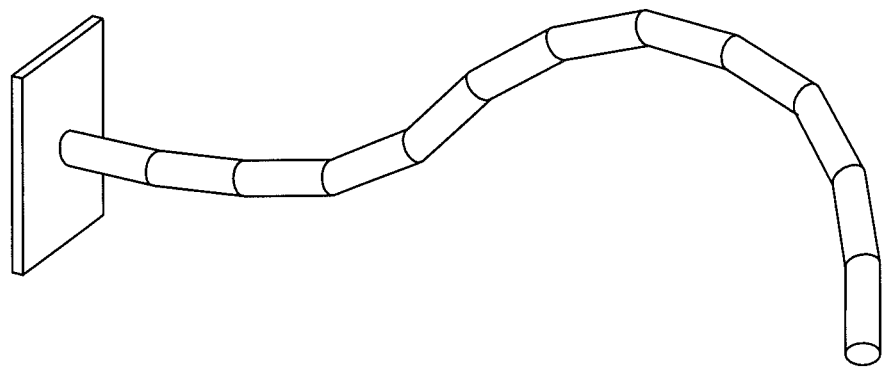
FIGS. 2A-2B illustrate various configurations assumed by a highly articulated probe, in accordance with the present inventive concepts.
Figure 2B:
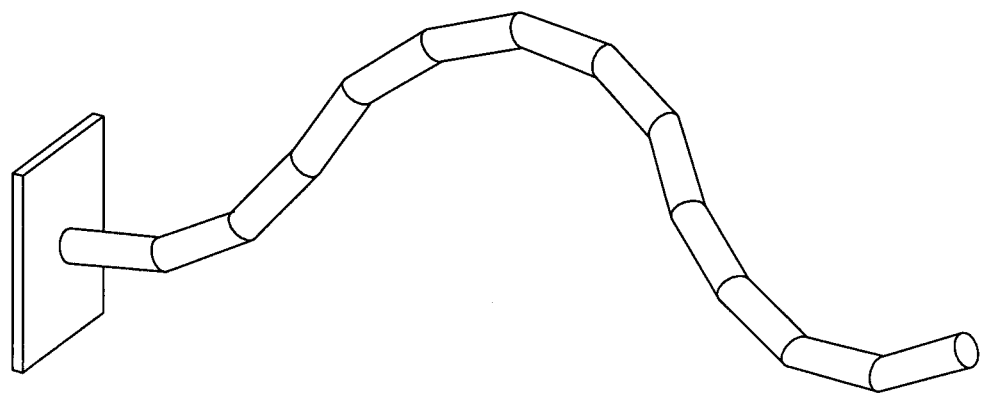
Figure 3A:
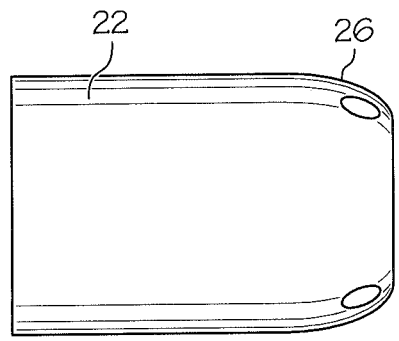
FIGS. 3A-3D illustrate various views of a link of an outer sleeve, in accordance with the present inventive concepts.
Figure 3B:
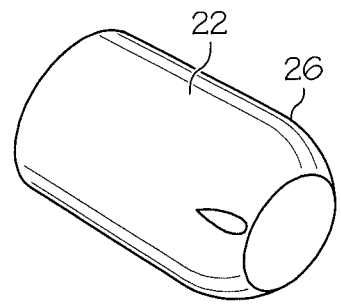
Figure 3C:
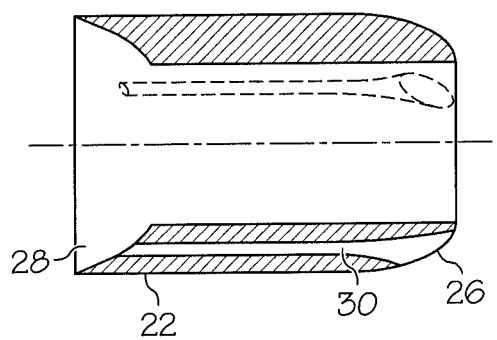
Figure 3D:
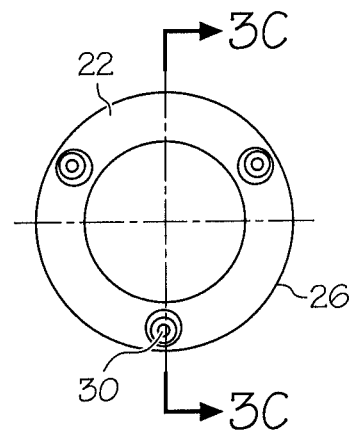
Figure 4B:
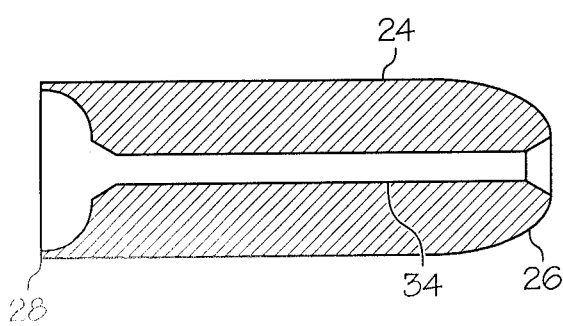
FIGS. 4A and 4B illustrate end and cross-sectional views, respectively, of a link of an inner core, in accordance with the present inventive concepts.
Figure 4A:
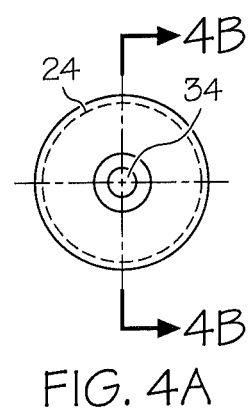

Inner core 12 and/or outer sleeve 14 are steerable and inner core 12 and outer sleeve 14 can each be made both rigid and limp, allowing probe 10 to drive anywhere in three-dimensions. Probe 10 can "remember" its previous configurations and for this reason, probe 10 can go anywhere in a three dimensional volume such as the intracavity spaces in the body of a patient such as a human patient. FIGS. 2A-2B illustrate examples of various configurations assumable by probe 10.

As can be seen in FIGS. 3A-3D and 4A and 4B, according to one embodiment, the outer sleeve 14 and inner core 12, respectively, can be made up of concentric cylinders, links 22, 24, respectively, although links of other shapes may be used, e.g. a dog bone configuration (not shown) as well as links of a type that are not concentric, e.g. backbone configuration, among others. The ends of the links 22, 24 are not flat but instead one end 26 is an "outer" or convex hemisphere and the other end 28 is an "inner" or concave hemisphere, both typically with similar radius of curvature. The links 22, or links, of the outer sleeve 14 are "chained" back-to-back such that the concave end 28 of one mates with the convex end 26 of an adjacent link. Similarly, the links 24, or links, of the inner core 12 are chained back-to-back. The result is a spherical-like joint, from a kinematic point of view. In the current embodiment, each link is able to rotate on the adjacent link's head, acting as a spherical joint with approximately 10-20 degrees range of motion in any direction, although other ranges of motion are possible and potentially advantageous. According to one embodiment, the links 22 have a plurality of channels 30 extending therethrough for control cables or elongate devices such as elongate tools.

The heads (i.e. the distal links) of either or both the outer sleeve 14 and the inner core 12 are steerable using three cables which are attached at, for example, 120° from each other. As can be seen in FIGS. 3A-3D, there are three small cylindrical channels 30, 32, respectively, for cables to pass through. In the version of the device shown in FIGS. 4A and 4B, the inner link 24 has only one cable, in which case there is only one hole 34 through its center.

It will be appreciated that although the embodiment described above utilizes cables such as conductive or non-conductive wires or other flexible filamentous structure, alternative means of manipulating the limp elements, such as miniature pneumatic or hydraulic pistons or other mechanical linkages situated between individual links, can be employed without falling outside the scope of the present inventive concepts.

The links, and hence probe 10, can be made out of virtually any material, including plastic or other magnetic resonance imaging compatible material. The outer sleeve 14 may assume a broad range of diameters, typically greater than 5 mm. Similarly, inner core 12 may assume a broad range of diameters, less than the diameter of outer sleeve 14 and typically more than 3 mm. The total number of links can vary over a large range but is typically greater than 10 links.

As noted, the inner core 12 and outer sleeve 14 can be made rigid or limp using cables or other flexible filament structures. In one embodiment, outer sleeve 14 consists of a set of links 22 strung on three cables. The three cables are typically 120 degrees apart, making it possible to steer in any direction. Radius of curvature of probe 10 is dependent on a number of factors including length of links 22 as well as mating dimensions between the ends of mating links 22. When the cables are pulled toward the back of the outer sleeve 14, the links 22 are pulled toward each other. When the pulling force increases, the friction force between adjacent links 22 increases until the entire outer sleeve 14 stiffens (i.e. enters the rigid mode). When the pulling force is released, the outer sleeve 14 becomes limp. Thus, the cables together with their respective tensioning assemblies (e.g. motor driven pullies) form a locking device. The tensioning assemblies, along with the electronics for controlling the tensioning assemblies, comprise a means for controlling the tension on the cable. When the outer sleeve 14 is positioned one link in front of the inner core 12, and the inner core 12 is stiff, the distal link of the outer sleeve 14 can be oriented by pulling one or more of the three cables. In addition to advancing or retracting cable, the magnitude of the pulling force which is exerted on each cable can be monitored or controlled. By pulling the three cables with the same magnitude, the outer sleeve 14 becomes stiff without changing its shape.

The inner core 12, like the outer sleeve 14, consists of a set of links. According to one embodiment, in contrast to the outer sleeve 14, the inner core 12 does not need (but may optionally have) a steering ability. The inner core 12 does need the ability to change from rigid mode, to limp mode, and back. Therefore, in embodiments where the inner core 12 need not be steerable, the links of the inner core 12 may be strung on a single cable, which enables a reduced overall diameter for probe 10.

Overview of Feeding Mechanism

Figure 5A:
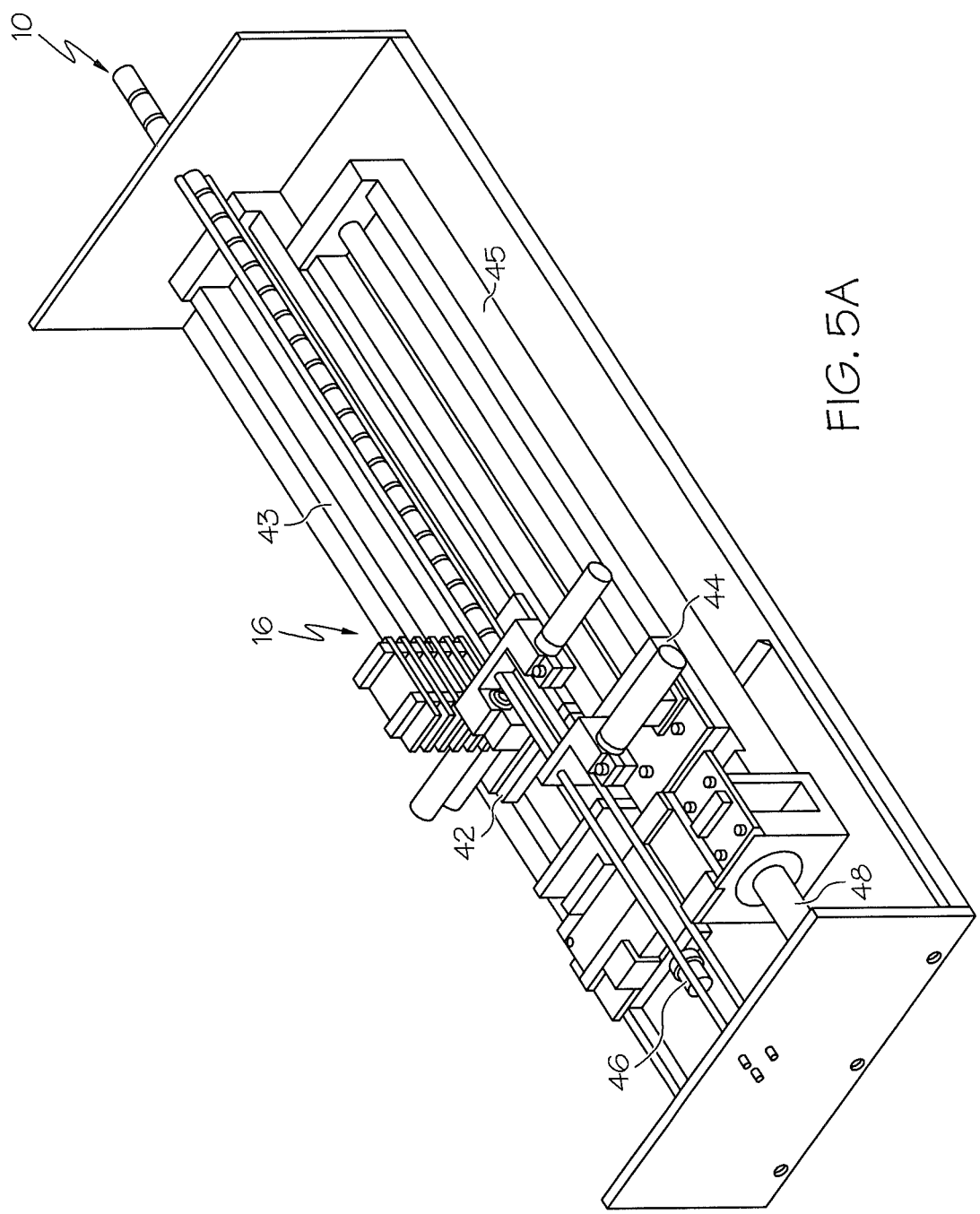
FIGS. 5A and 5B illustrates one example of a feeder mechanism, in accordance with the present inventive concepts.
Figure 5B:
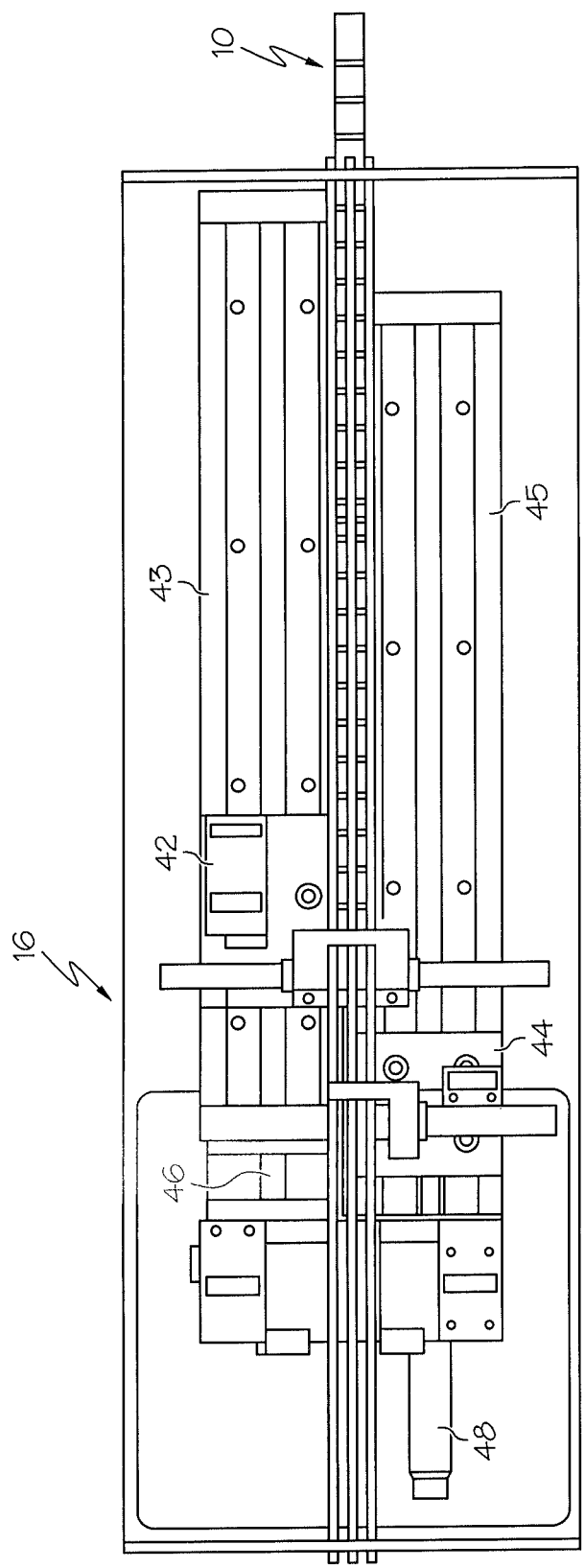

As mentioned above, a feeding mechanism 16 can be used to control the probe 10. One type of feeding mechanism 16, shown in FIGS. 5A and 5B, inserts and retracts the probe 10 into and out of, respectively, a region of interest such as the esophagus, the peritoneal space, the pericardial cavity, or another internal space of a patient. The feeder 16 has two movable carts. A first cart 42, carried in a first fixed tray 43, advances and retracts the outer sleeve 14 while a second cart 44, carried in a second fixed tray 45, advances and retracts the inner core 12. Each cart 42, 44, and hence each of the inner core 12 and outer sleeve 14, is driven independently by separate linear actuators 46, 48 respectively. The linear actuators 46, 48 may carry shaft encoders (not shown) used for position control as is known. Alternatively or additionally, motor current may be monitored to determine a value for tension in a cable used to control position. Cable tension may be monitored with one or more sensors such as a load cell. Numerous positioning and other sensors may be included to provide information relative to cable tension; cart position; probe orientation and configuration; and other system parameters. Typical sensors include but are not limited to: optical sensors; magnetic sensors such as Hall effect sensors; force and pressure sensors such as accelerometers, strain gauges and mechanical switches; and combinations of these. One or more sensors may be positioned in multiple locations including but not limited to: feeding mechanism 16, inner core 12 and outer sleeve 14.

Figure 7:
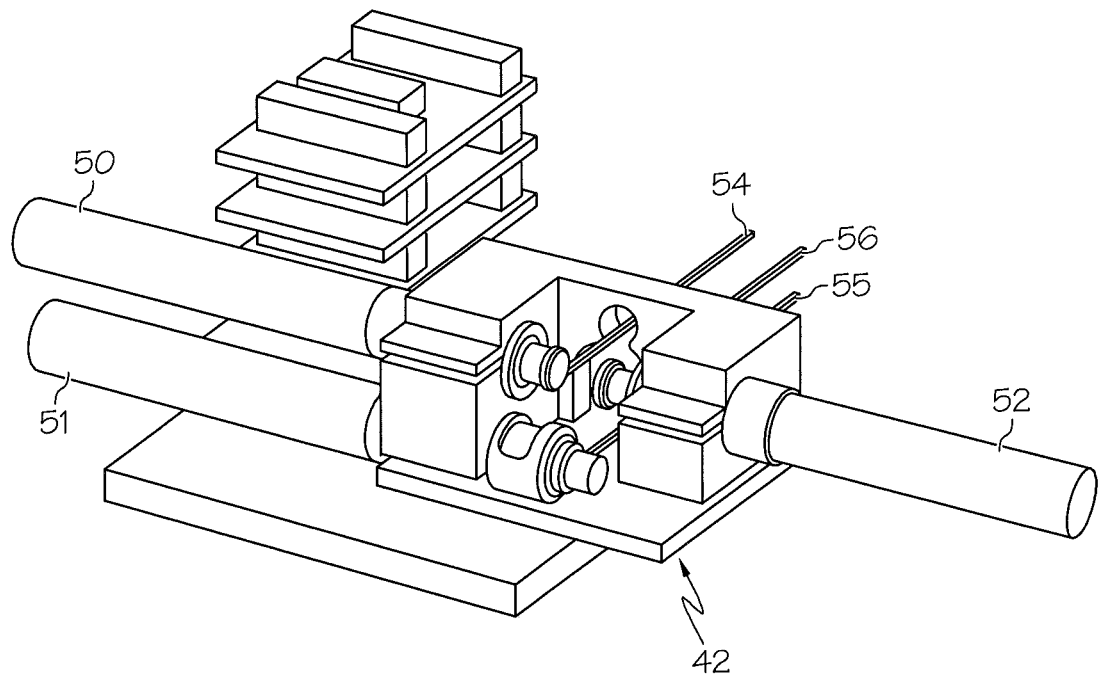
FIG. 7 illustrates devices for controlling the tension on the cables of the outer sleeve, consistent with the present invention.
Figure 8:
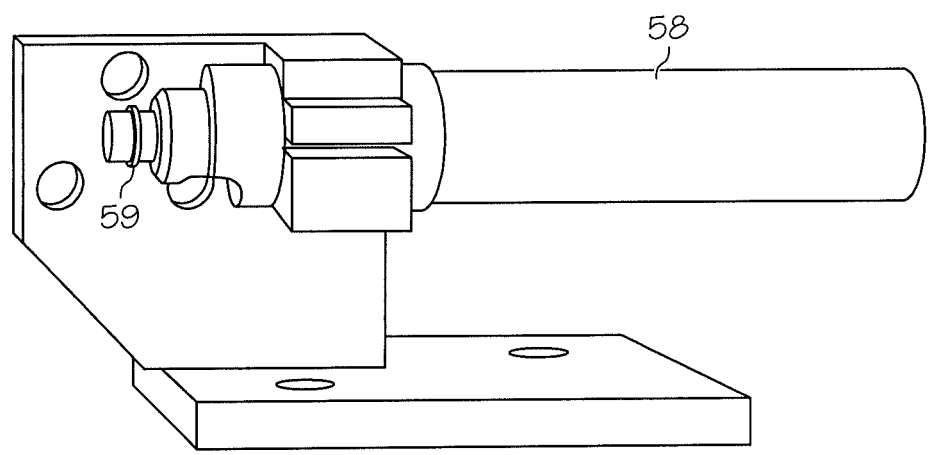
FIG. 8 illustrates a device for controlling the tension on the cable of the inner sleeve, in accordance with the present inventive concepts.

Each of the carts 42, 44 carries one or more motors necessary for controlling the cables of the inner core 12 and outer sleeve 14. For example, as seen in FIG. 6 and FIG. 7, the cart 42 carries motors 50, 51, 52 which control the tension on cables 54, 55, 56 of outer sleeve 14. As shown in FIG. 8, second cart 44 has a motor 58 for controlling the tension on cable 59 of the inner core 12. Each of the motors 50, 51, 52 and 58 may be provided with shaft encoders (not shown) used for position control as is known. In an embodiment where the inner core 12 is steerable, the inner core 12 requires two or more motors (e.g. to tension two or more cables) or another cable tensioning mechanism.

Figure 9:
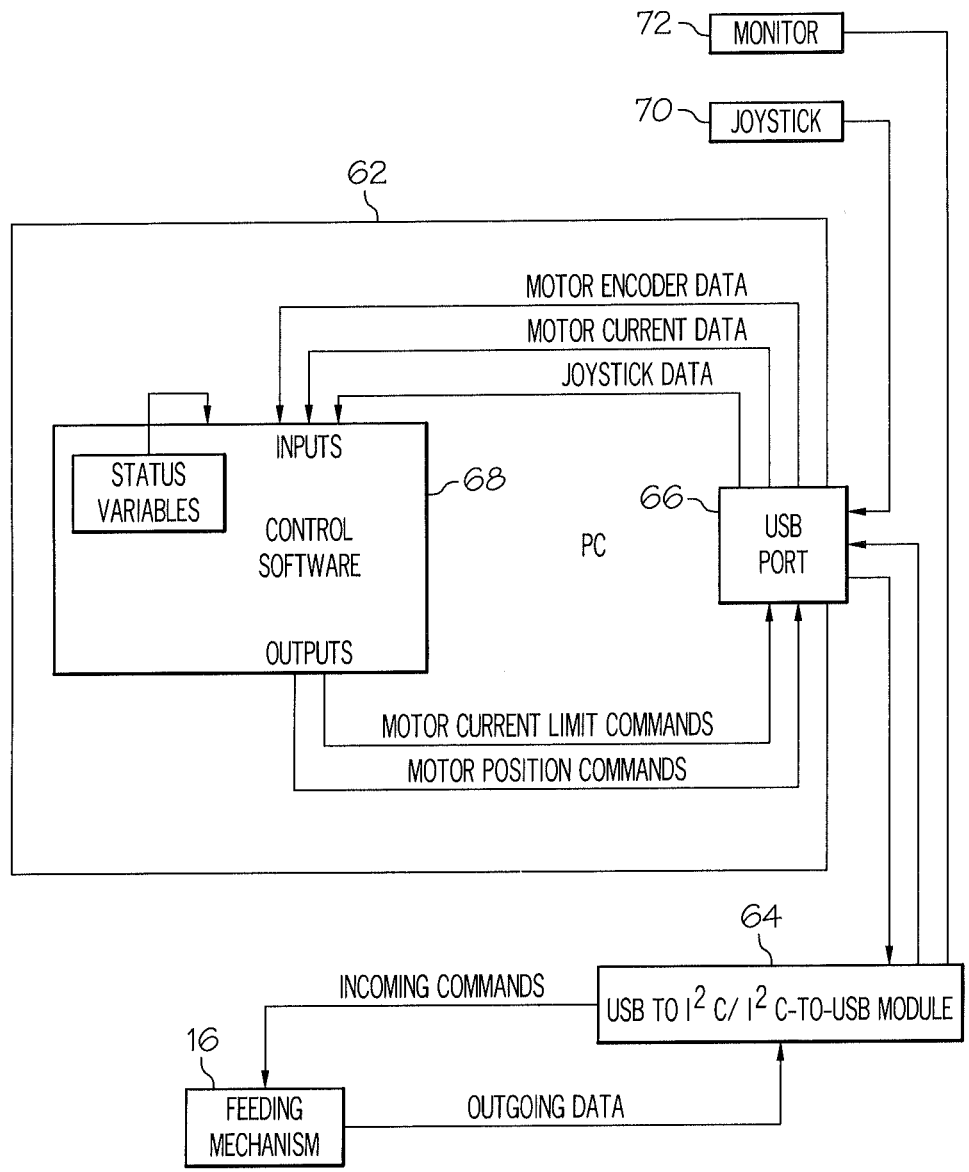
FIG. 9 is a block diagram illustrating the components of a control system and the flow of information between those components, in accordance with the present inventive concepts.
Figure 10A:
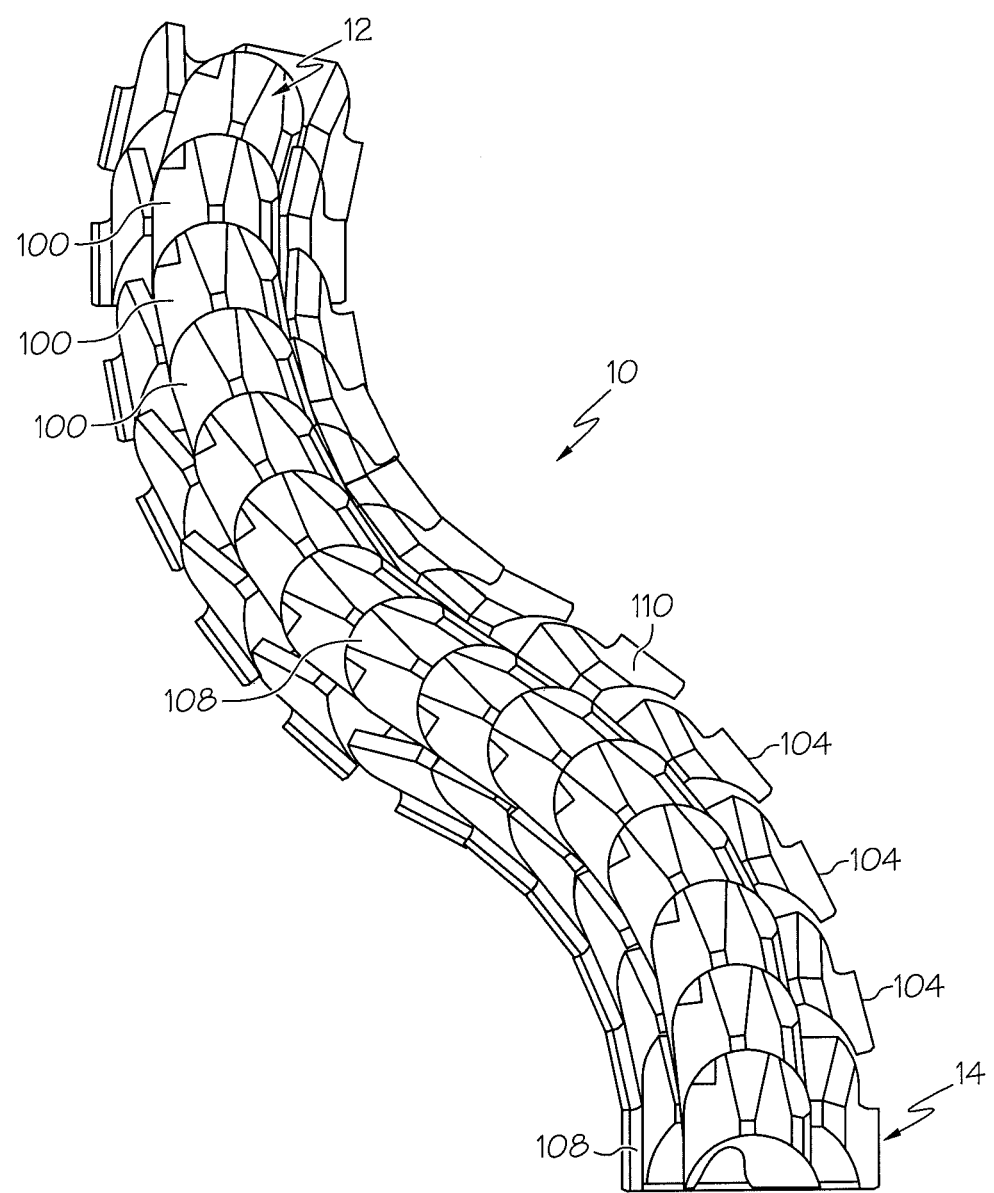
FIGS. 10A and 10B illustrate a cross section of an articulated probe according to an embodiment, in accordance with the present inventive concepts.
Figure 10B:
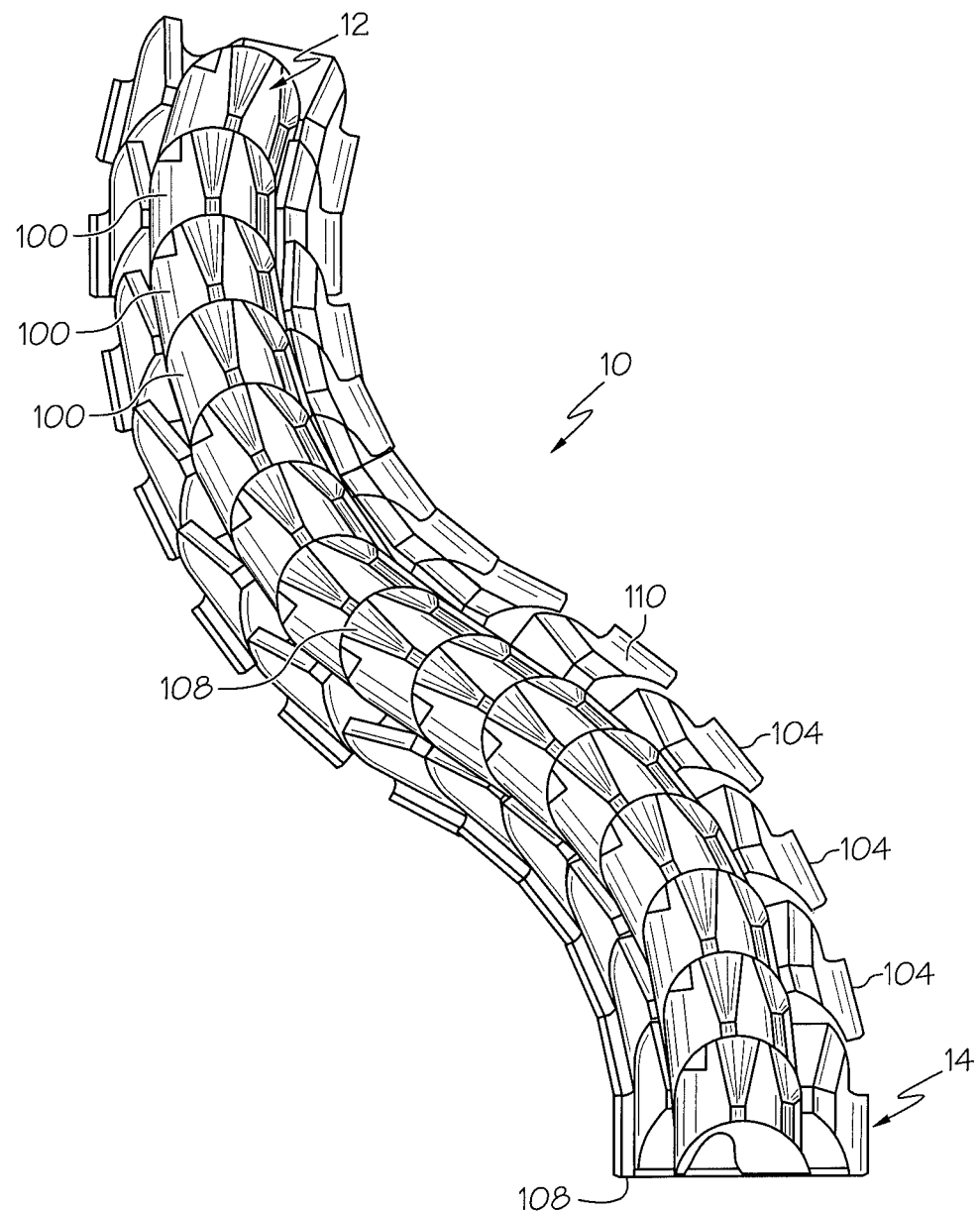

FIG. 9 is a block diagram illustrating the components of one embodiment of a control system and the flow of information between those components. The feeding mechanism 16 interfaces with a control computer 62 through a bus conversion module 64. Outgoing data from the feeding mechanism 16 is input to the module 64 for conversion to the USB and is then input to a USB port 66 on the computer 62. Incoming data to control software 68 may include motor current data, motor encoder data and/or cable tension data associated with each of the cables in the feeding mechanism 16. Alternatively or additionally, incoming data to control software 68 may include data from one or more sensors located in feeding mechanism 16, inner core 12 or outer sleeve 14. Joystick data (position data) may also be received from a joystick 70. A monitor 72 may be responsive to video data from a camera mounted on the distal end of the outer sleeve 14 and/or inner core 12 to provide visual feedback to a user regarding the position of the distal end of the probe 10. The control software 68 may output motor current limit commands and motor position commands which are input to the feeding mechanism 16.

Inner Core and Outer Sleeve

FIGS. 10A-11B illustrate an embodiment of the articulated probe 10 with the inner core 12 and the outer sleeve 14. The inner core 12 has a plurality of inner links 100 (preferably at least three, and, in some embodiments, fifty or more). The outer sleeve 14 has a plurality of outer links 104 (preferably at least three, and, in some embodiments, forty or more).

Figure 11A:
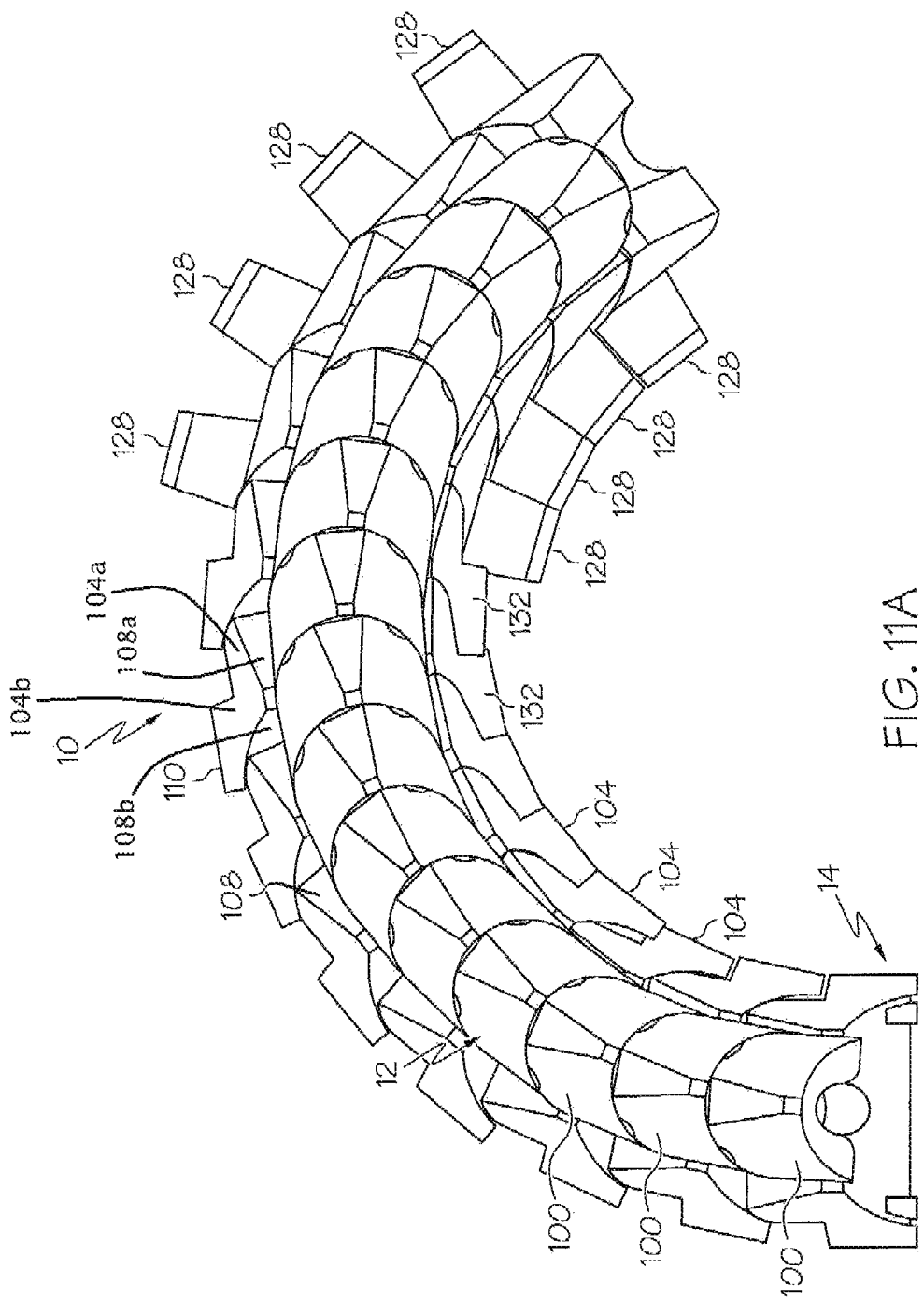
FIGS. 11A and 11B illustrate a cross section of an articulated probe according to an embodiment, in accordance with the present inventive concepts.
Figure 11B:
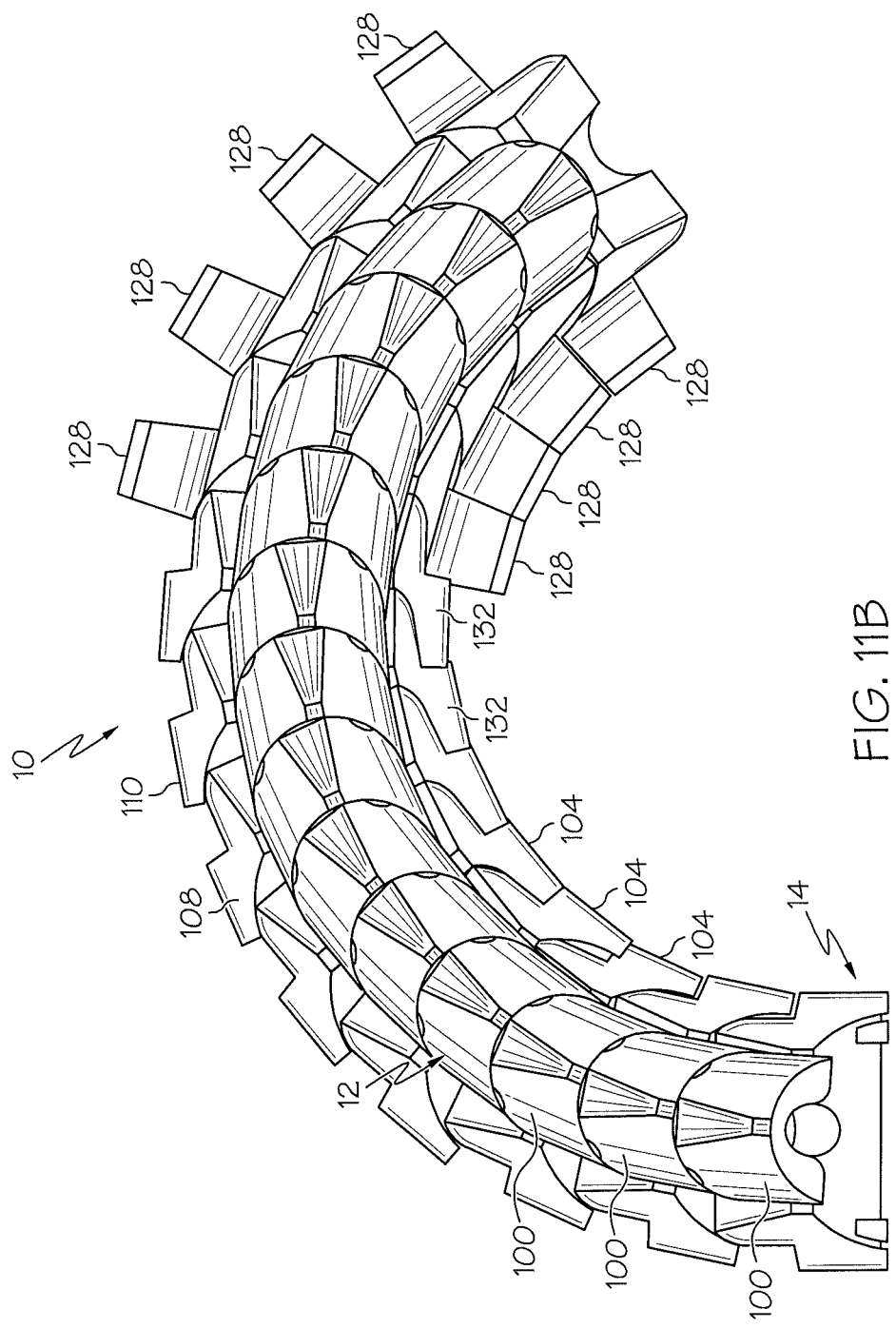

With regard to the outer links, FIGS. 14A-16J illustrate various views of presently preferred embodiments of such outer links 104, 132. These embodiments of the outer links are similar to those discussed in the overview above. However, these embodiments differ in some significant aspects from those discussed above, as well as from each other. The present embodiments of the outer links 104, 132 can be combined to form a unique outer sleeve 14, such as shown in FIG. 11A. In particular, FIGS. 16A-16K illustrate various views of outer links 104 with tool side ports 128. The tool side ports 128 can be used to receive and guide tools. FIGS. 15A-15J illustrate various views of transition outer links 132. As shown in FIG. 11A, a plurality of transition outer links 132 can be positioned adjacent an outer link 104 with tool side ports 128. The transition outer link 132 can have one or more recesses 130 that accommodates and funnels elongated members, such as tools, into the tool side port 128 of the outer link 104. For example, the inner diameter of the outer link 104, 132 preferably is in the range of 0.10-2.00 inches, and more preferably the inner diameter, is approximately 0.394 inches. The outer diameter of the outer link 104, 132 preferably is in the range of 0.20-3.00 inches, and more preferably the outer diameter is approximately 0.669 inches. The outer link 104, 132 may be comprised, for example, of at least one of metals, plastics, glass, carbon fiber, etc. In a particular embodiment, the outer link 104, 132 is comprised, for example, of polyphenylsulfone (e.g., Radel® R-5100).

With regard to the inner links 100, FIGS. 17A-17I illustrate various views of presently preferred embodiments. These inner links 100 are similar to those discussed in the overview above. However, they differ in some significant aspects. The length of the inner link 100 preferably is in the range of 0.01-2.00 inches, and more preferably the length of the inner link 100 is 0.353 inches. The outer diameter of the inner link preferably is in the range of 0.10-2.00 inches, and more preferably, the inner diameter is 0.354 inches. The inner link 100 may be comprised, for example, of at least one of metals, plastics, glass, carbon fiber, etc. In a particular embodiment, the inner link 100 is comprised of plastic with embedded glass fiber (30% by weight).

The inner links 100 are configured to pivot relative to one another through a maximum pivot angle, and the outer links 104 are configured to pivot relative to one another through a maximum pivot angle, as shown for example in FIGS. 10A-13B. Preferably, the maximum pivot angle of the inner links 100 is no less than the maximum pivot angle of the outer links 104. In view of this pivoting relationship, it can be important for the links 100, 104 to be configured in such a way to avoid one or more undesired conditions such as; limiting the articulated probe 10 flexion; pinching of an elongated member that may be positioned within the links 100, 104; and problems that might occur with the advancement and retraction of the elongated member.

Figure 14A:
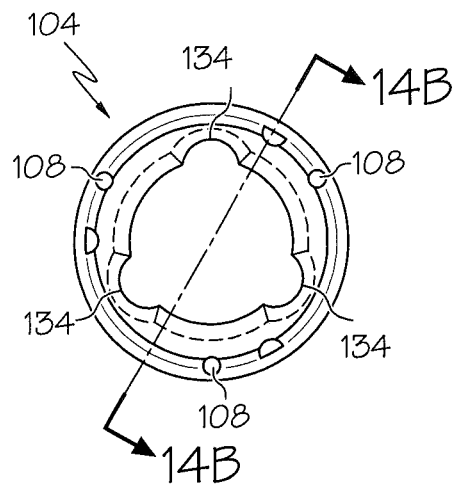
FIGS. 14A-14I illustrate various views of an outer link, according to an embodiment, in accordance with the present inventive concepts.
Figure 14B:
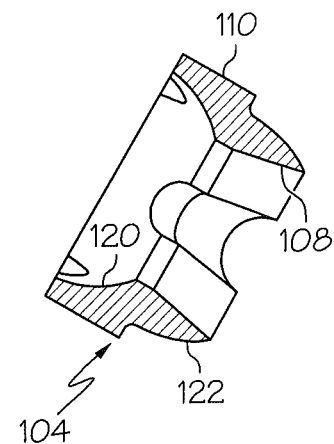
Figure 14C:
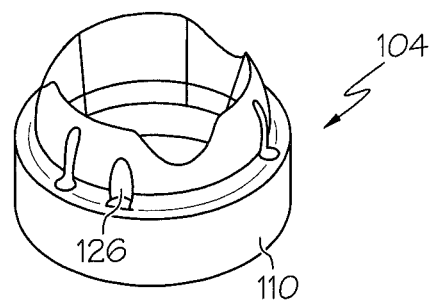
Figure 14D:
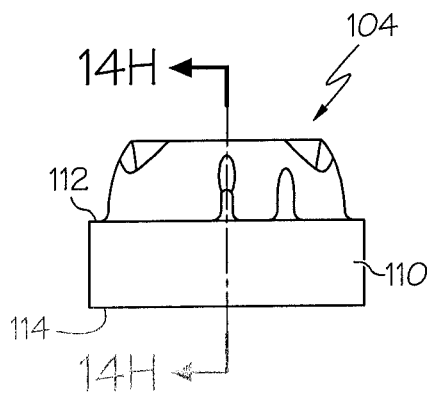
Figure 14E:
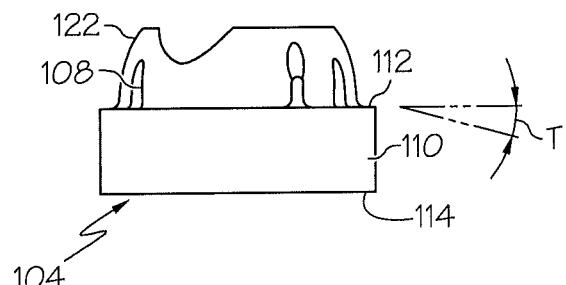
Figure 14F:
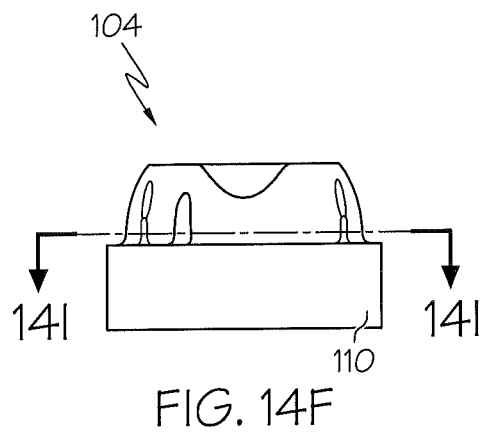
Figure 14G:
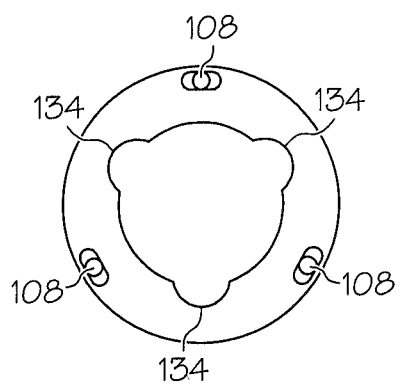
Figure 14H:
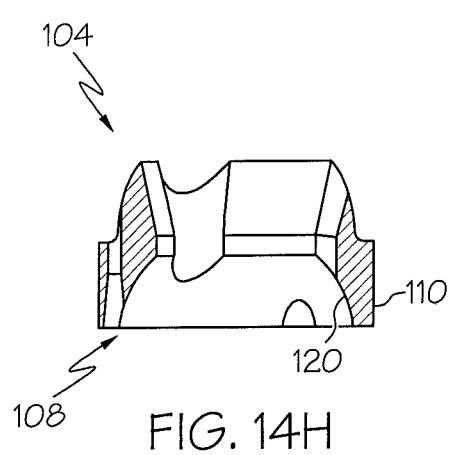
Figure 14I:
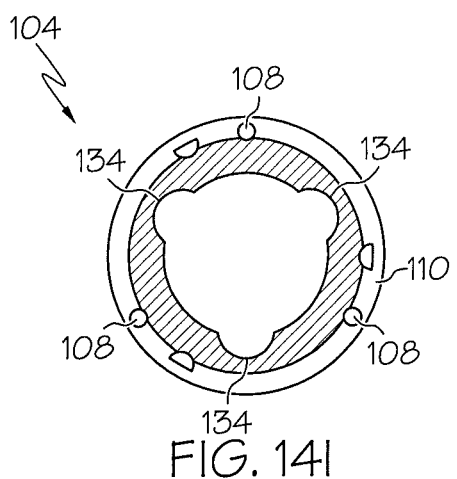
Figure 15A:
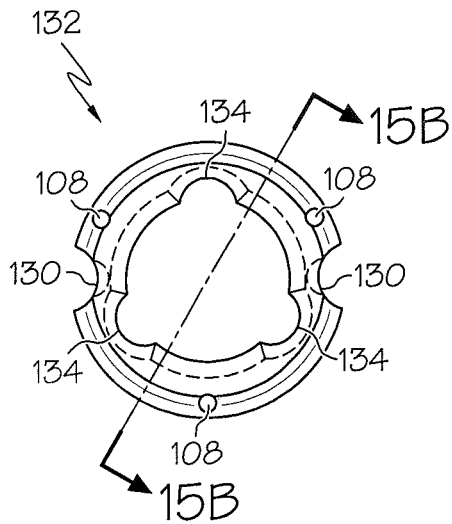
FIGS. 15A-15J illustrate various views of an outer link transition segment, according to an embodiment, in accordance with the present inventive concepts.
Figure 15B:
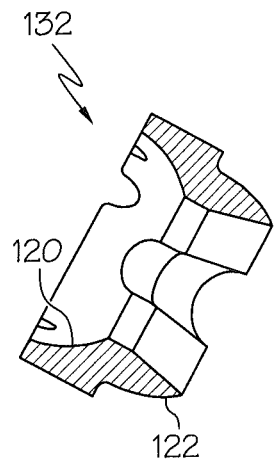
Figure 15C:
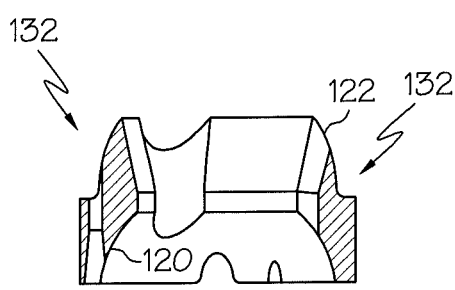
Figure 15D:
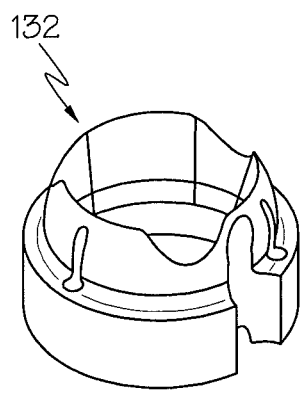
Figure 15E:
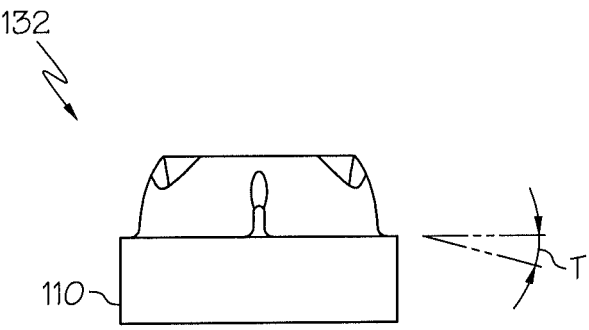
Figure 15F:
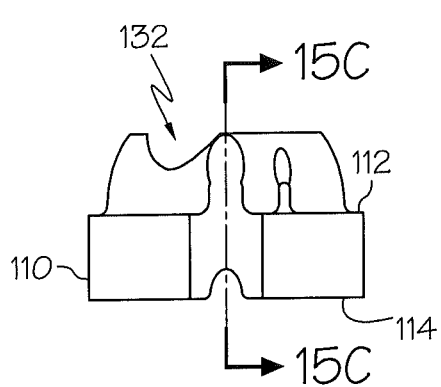
Figure 15G:
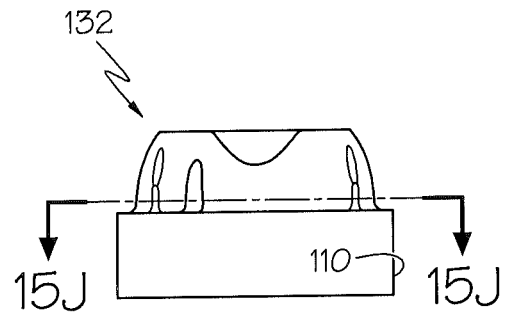
Figure 15H:
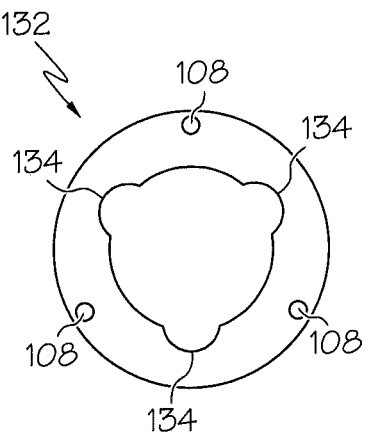
Figure 15I:
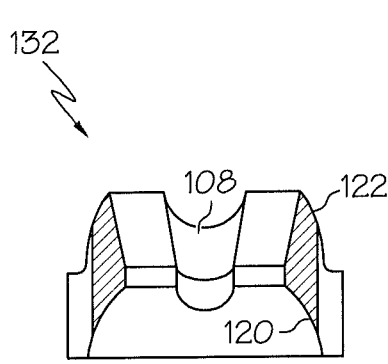
Figure 15J:
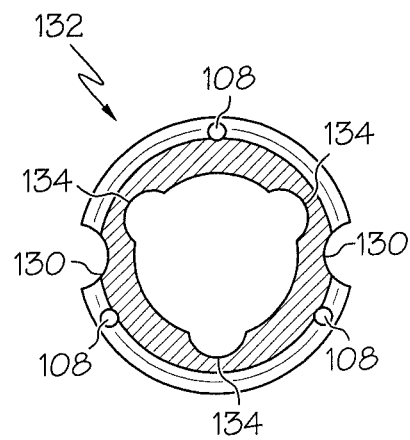
Figure 16A:
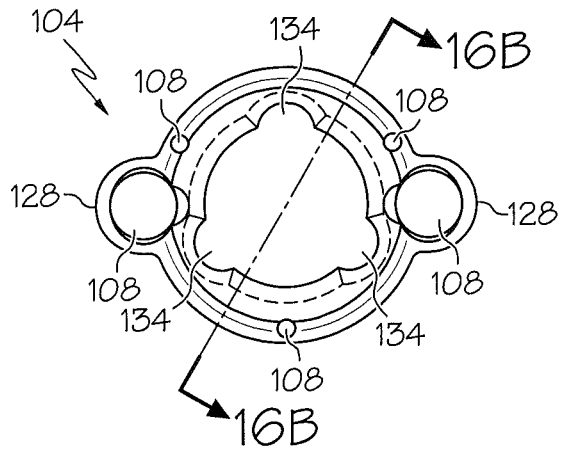
FIGS. 16A-16K illustrate various views of an outer link with tool side ports, according to an embodiment, in accordance with the present inventive concepts.
Figure 16B:
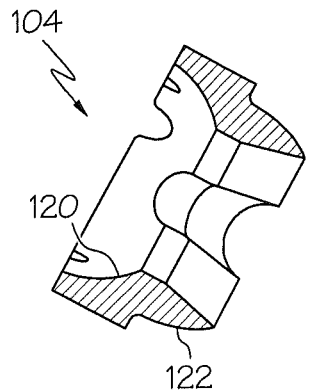
Figure 16C:
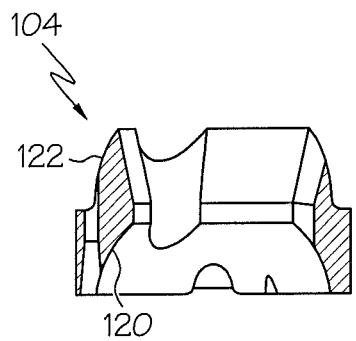
Figure 16D:
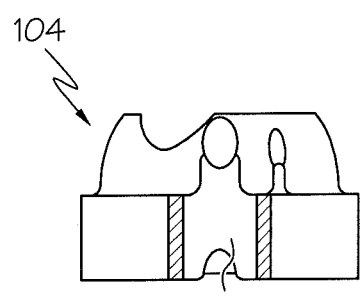
Figure 16E:
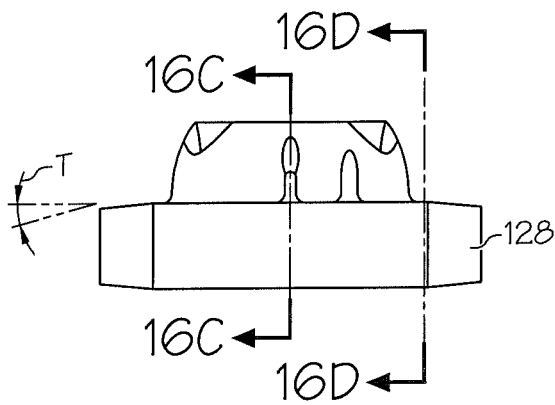
Figure 16F:
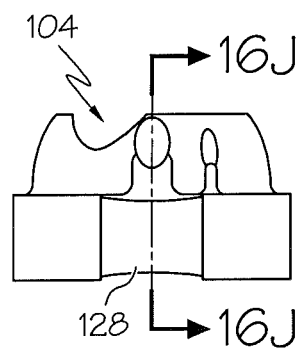
Figure 16G:
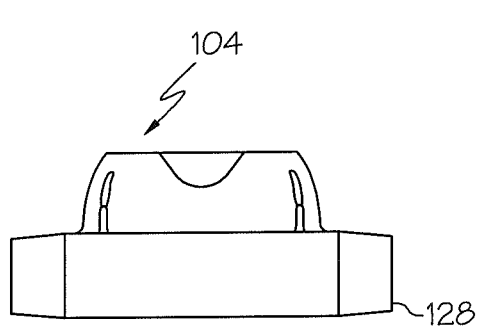
Figure 16H:
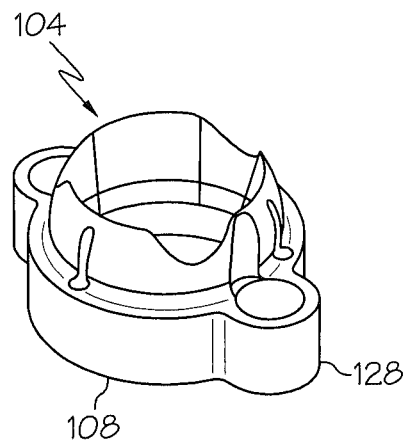
Figure 16I:
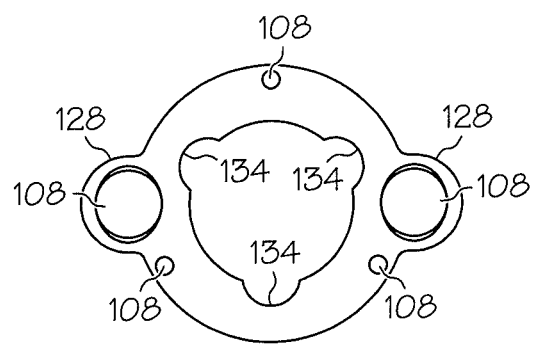
Figure 16J:
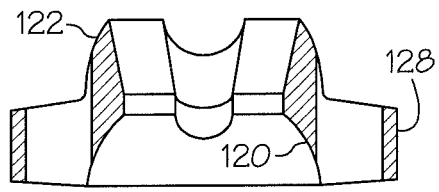
Figure 16K:
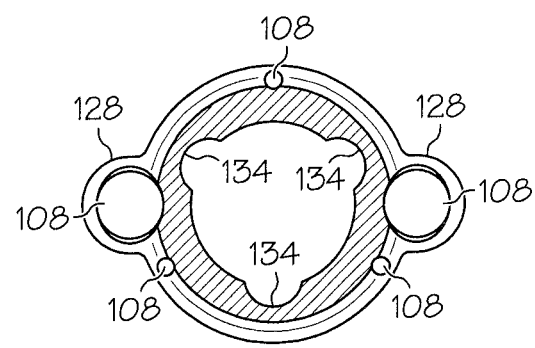
Figure 17A:
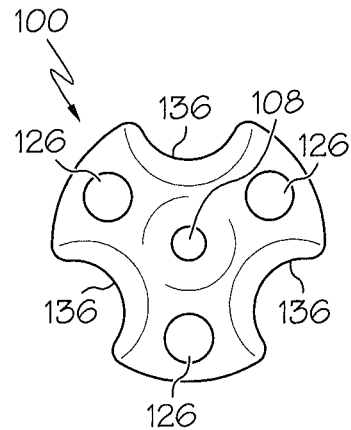
FIGS. 17A-17I illustrate various views of an inner link, according to an embodiment, in accordance with the present inventive concepts.
Figure 17B:
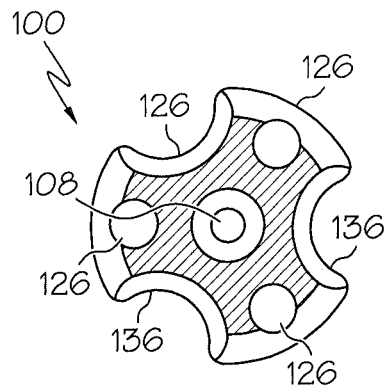
Figure 17C:
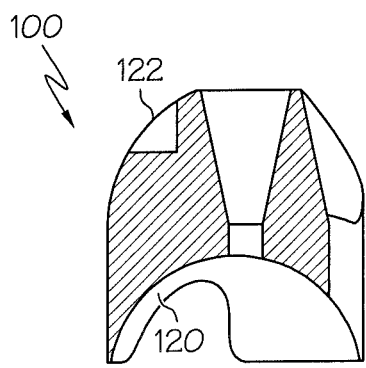
Figure 17D:
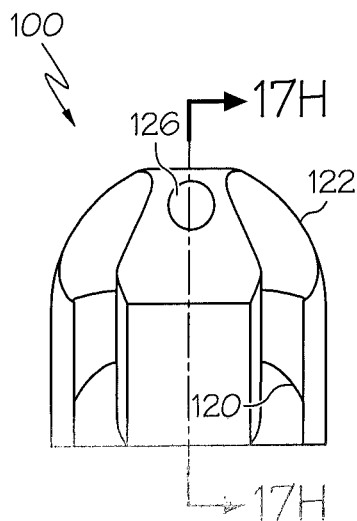
Figure 17E:
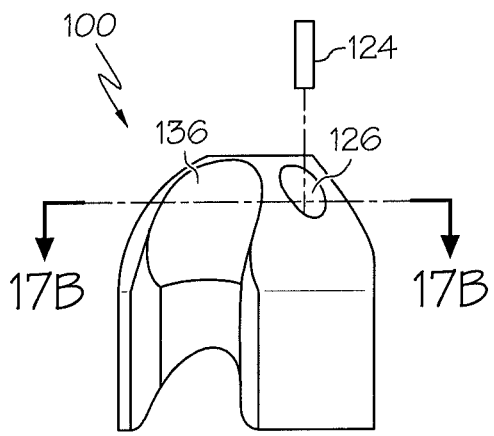
Figure 17F:
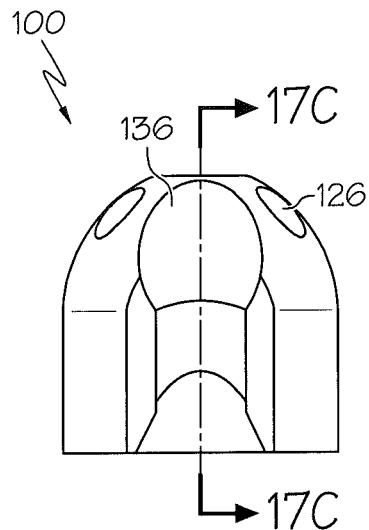
Figure 17G:
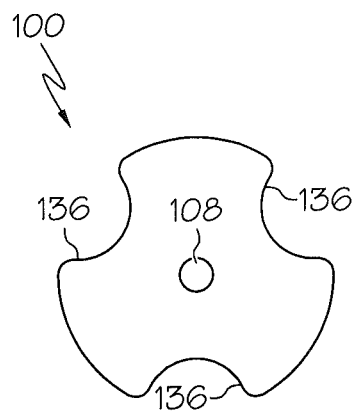
Figure 17H:
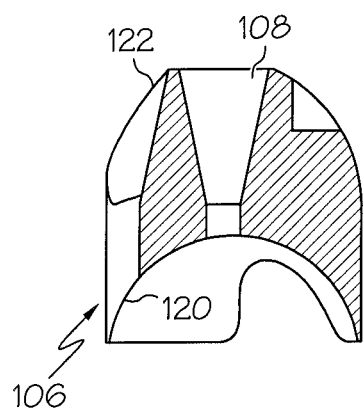
Figure 17I:
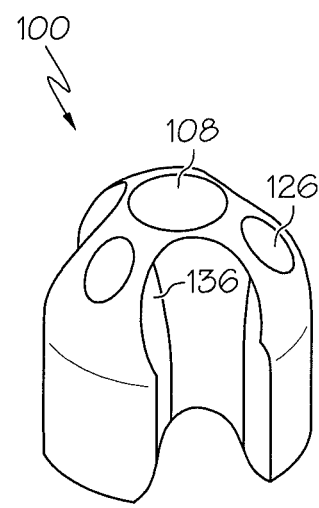
Figure 18:
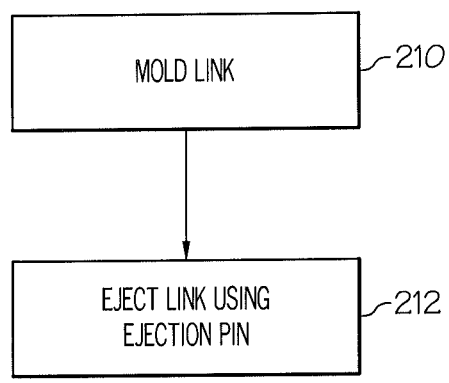
FIG. 18 is a flow chart for producing a link for an articulated probe according to an embodiment, in accordance with the present inventive concepts.

Each of the plurality of inner links 100 and/or outer links 104 may have one or more channels 108 for receiving an elongated member. Alternatively or additionally, mating recesses in inner links 100 and outer links 104 may create one or more channels between inner core 12 and outer sleeve 14. An elongated member may be any one of a tool, an inner cable 102, an outer cable 106, or an inner core 12. Typical elongate tools include but are not limited to: scissors, scalpels and other cutting tools; graspers such as tissue graspers; energy delivery elements such as tissue ablation elements, electrocautery and coagulation elements; cambers such as fiber optic cameras; heating elements; cooling elements; drug delivery devices; and combinations of these. As discussed in the overview, the tool can be used to perform various operations and one or more cables may be used to control the outer links 104 of the outer sleeve 14 and the inner links 100 of the inner core 12. The channels 108 are configured to form a semi-continuous passage from link 100, 104 to an adjacent link 100, 104 and can include a liner to facilitate reception of the elongated member. In some embodiments, as shown in FIG. 11A, a channel 108 of an outer link 104 includes a first portion 108a extending through a first portion 104a of the outer link 104 and a second portion 108b extending through a second portion 104b of the outer link 104. As shown in FIG. 14G, the channel 108 may have a circumferential flare. The circumferential flare avoids pinching elongated members within the channel 108 and facilitates rotation of the plurality of links 100, 104 while significantly reducing any difficulty that may be encountered by advancing or retracting an elongated member through the probe 10. Further, the channels 108 of inner links 100 and/or outer links 104 may be tapered to achieve a semi-continuous passage from link 100, 104 to link 100, 104.

According to one embodiment, the channel 108 in each of the inner links 100 and/or outer links 104 is tapered in an amount sufficient to permit the inner links 100 and/or outer links 104 to pivot through the maximum pivot angle while providing a substantially continuous surface between the channels 108 of the links 100, 104 for receiving the elongated member. More preferably, the opening and/or exit of the channel 108 can be tapered. The tapered openings and exits of the channel 108 avoid pinching elongated members within the channel 108 and significantly reduce any difficulty that may be encountered by advancing or retracting an elongated member through the probe 10. In addition, the tapered openings correlate to the radius of curvature of probe 10. According to one embodiment, the taper of the channel 108 is approximately twice the maximum pivot angle. For example, the taper can be approximately 26° degrees and the maximum pivot angle can be approximately 13° degrees. The taper of the channel 108 preferably can accommodate a pivot angle of 13° degrees or greater. In sum, the tapered channels 108 are configured to provide a substantially continuous surface between the channels 108 of the links 100, 104 for the reception of the elongated member.

The inner links 100 of the inner core 12 may have the channel 108 positioned near a central axis and configured to receive an inner cable 102 (the elongated member), as shown in FIGS. 13A-B and 17A-17I. The channel 108 within the inner links 100 can have a flared opening. According to one embodiment, the flared opening is positioned off-center in relation to the central axis of the inner link 100. Positioning the flared opening off-center allows the pivot point of the inner cable 102 to change more easily when the pivot point of the inner core 12 may change due to rotation of the inner core 12 or any other form of translational displacement that may occur. Preferably, the diameter of the channels 108 of the inner links 100 is greater than the diameter of the inner cable 102, which reduces the occurrence of twisting and sawtoothing of the inner links 100. For example, if the channel 108 preferably has a diameter in the range of 0.003-0.500 inches (more preferably approximately 0.043 inches), the diameter of the inner cable 102 preferably is in the range of 0.002-1.000 inches (more preferably approximately 0.037 inches). By configuring the diameter of the inner cable 102 and channel 108 of the inner links 100 to reduce twisting and sawtoothing, the likelihood of pinching or difficulty with advancement and retraction of the elongated member is also significantly reduced. Thus, the channel 108 of the inner link 100 provides a substantially continuous surface between links 100 for the inner cable 102.

Figure 12A:
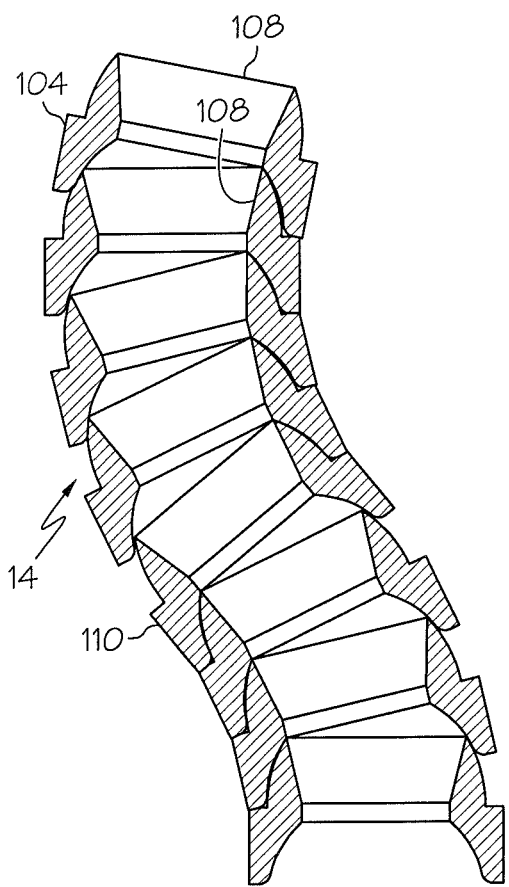
FIGS. 12A-12B illustrate a cross section of an outer sleeve according to an embodiment, in accordance with the present inventive concepts.

The outer links 104 of the outer sleeve 14 also may have the channel 108 formed therein for the reception of an elongated member, as shown for example in FIG. 12A. In this particular embodiment, the elongated member can be an inner core 12 with a plurality of inner links 100. The channel 108 includes a plurality of outer links 104, each having a flared opening. As shown in FIG. 12A, the flared opening in each of the plurality of links 104 provide a substantially continuous surface between links 104 for reception of the inner core 12. The channels 108 of the outer links 104 are also tapered in an amount sufficient to permit an inner core 12 to pivot through a maximum pivot angle while providing a substantially continuous surface between the channels 108 for the inner core 12. The taper of the channels 108 also allows flexion of the inner links 100. Preferably, the inner flexion of the inner links 100 may be greater than or equal to 13° degrees. Thus, the channel 108 of the outer link 104 provides a substantially continuous surface between links 104 for the reception of the inner core 12.

A plurality of channels 108 also may be positioned near the outer surface of the outer link 104, as shown in FIGS. 14A-16K. According to one embodiment, three channels 108 are positioned approximately 120° degrees from each other around a circumference of one or more outer links 104 making up the outer sleeve 14. The channels 108 of the outer link 104 are configured to receive an elongated member in the form of outer cables 104 for controlling the outer sleeve 14. Preferably, a diameter of the outer cables 106 is less than a diameter of the channels 108 of the outer links 104, which reduces the occurrence of twisting and sawtoothing of the outer links 104. According one embodiment, the diameter of the outer cables 106 may be in the range of 0.002-1.000 inches. In one embodiment, the diameter of outer cables 106 is 0.027 inches. The diameter of the channels 108 in each outer link 104 for receiving the outer cables 106 may be in the range of 0.003-0.500 inches. In a particular embodiment, the diameter of the channels 108 in each outer link 104 are approximately 0.035 inches. By configuring the diameter of the outer cables 106 and channels 108 of the outer links 104 to reduce twisting and sawtoothing, the likelihood of pinching or difficulty with advancement and retraction of the elongated member is also significantly reduced. Thus, the channels 108 of the outer link 104 provides a substantially continuous surface between links 104 for the plurality of cables 106.

A combination of the inner link 100 and the outer link 104 also may be configured so as to provide the channel 108 for receiving an elongated member. With reference to FIGS. 14A-14I, an inner surface of the outer link 104 can have a flared indentation 134 which forms one half of a channel 108 for receiving an elongated member in the form of a tool. As shown in FIGS. 17A-17I the other half of the channel 108 is formed by flared indention 136 on the outer surface of the inner link 100. The channel 108 formed by the flared indention 136 of the inner link 100 and the flared indention 134 of the outer link 104 provides a substantially continuous surface between links 100, 104 for one or more tools.

The outer links 104 and 132 shown in FIGS. 15A-16K can both be configured to receive an elongated member in the form of a tool, cable, or other elongated device. With respect to FIGS. 11A and 16A-16K, the channels 108 of an outer link 104 can be formed by tool side ports 128. The tool side ports 128 extend out from the outer circumference of the outer link 104 and are configured with a channel 108 to receive tools, cables, or other elongated devices. As shown in FIG. 11A, the transition outer link 132 is positioned between an outer link 104 and an outer link 104 with tool side ports 128 along the length of the probe 10. According to one embodiment and as shown in FIGS. 15A-15J, the transition outer link 132 has one or more recesses 130 that accommodates and funnels tools into an outer link 104 having a tool side port 128. Accordingly, tools configured for use approximately outside the circumference of the probe 10 can be received by the channels 108 formed by the tool side ports 128 and the recesses 130 of the transition outer link 132. The channels 108 formed by the tool side ports 128 and the recesses 130 provides a substantially continuous surface between the outer links 104, 132 for one or more elongate devices.

The radius of curvature of the articulated probe 10 can depend on the pivot angle of the inner and outer links 100, 104. With respect to FIGS. 10A-12B and 14A-I, the outer sleeve 14 may include a plurality of outer links 104 having an outwardly extending flange 110. The flange 110 is configured to control the pivot angle of the outer links 104 relative to one another. Thus, characteristics of the flange 110 impact the radius of curvature of the articulated probe 10 that can be achieved.

According to one embodiment, the geometry of the flange 110 determines the degree of pivot possible between each of the outer links 104. With respect to FIGS. 14D-14E, the flange 110 can have a first engagement surface 112 and a second engagement surface 114 extending radially outward relative to a first central axis of the outer link 104. The flange 110 is configured to permit the outer links 104 to pivot relative to one another and a probe central axis through an outer maximum pivot angle until the first engagement surface 112 of a first outer link 104 and the second engagement surface 114 of a second outer link contact each other. According to one embodiment, the first engagement surface 112 and the second engagement surface 114 taper relative to a line perpendicular to a central axis of the outer link 104. With reference to FIG. 14E, in one particular embodiment, the first engagement surface 112 tapers approximately 6.5° degrees and the second engagement surface 114 tapers approximately 6.5° degrees. According to this embodiment, the outer maximum pivot angle is no greater than approximately 13° degrees. In alternative embodiments, the taper of the first engagement surface 112 and the second engagement surface 114 may be configured so that the maximum pivot angle is greater that 13° degrees, or less than 13 degrees. Preferably, the geometry of the flange 110 is configured so that the radius of curvature of the articulated probe 10 is in the range of 10-600 mm. Thus, the geometry of the flange 110 can be used to set the maximum pivot angle of the outer links 104, which in turn impacts a range of the radius of curvature of the articulated probe 10.

The links 100, 104, 132 can be configured to reduce the occurrence of irregular or undesired forces (e.g. irregular or undesired frictional engagement forces) acting between a first and second link 100, 104. For example, as shown in FIGS. 14B, 14H, 15B, 15C, 15I, 16B, 16C, 16J, 17C, 17D, 17H, the plurality of inner links 100 and outer links 104 may include a first concave portion 120, also referred to as a second portion, and a first convex portion 122, also referred to as a first portion. A convex portion 122 of a first link 100, 104 can pivotally engage a corresponding concave portion 120 of a second link 100, 104. According to a particular embodiment, the first link 100, 104 convex portion 122 has a radius of curvature no greater than a radius of curvature of the second link 100, 104 concave portion 120. The links 100, 104 can be linked together to form an inner core 12 and outer sleeve 14. The arrangement of the links 100, 104 (a concave portion 120 pivotally engaging a corresponding convex portion 122) allows the inner core 12 and outer sleeve 14 to pivot with a wide range of motion and reduces the occurrence of irregular or undesired frictional or other forces between links 100, 104 that may interfere with efficient operation of the articulated probe 10.

As demonstrated above, the physical characteristics of the various features of the inner core 12 and outer sleeve 14 affect the properties and performance of the articulated probe 10 in various ways. According to one embodiment, the geometric dimensions of one or more channels of an outer link 104 are mathematically related to one or more parameters of outer link 104. These parameters may include: the radius of an end of outer link 104; the diameter of outer link 104; the pivot angle between outer links 104; diameter of the channel such as average diameter of the channel; the channel location such as the distance of the channel from a central axis of outer link 104.

It can be advantageous to form the links in a way that facilitates smooth articulation of one link relative to the other and avoids undesired mating forces such as irregular frictional engagement between adjacent links. With respect to FIGS. 17A, 17B, 17D-17F, 17I and 18 a method for producing a link 100, 104 for an articulated probe 10 will now be described. In step 210, the link 100, 104 is molded in a molding device, including forming at least one engagement surface configured to engage an adjacent link 100, 104 in the articulated probe 10. In step 212, the link 100, 104 is ejected from the molding device by pressing at least one ejection pin 124 (see FIG. 17E) against an ejection surface 126 of the link 100, 104 that will not engage an adjacent link 100, 104 in the articulated probe 10. As shown in FIGS. 17A, 17B, 17D-E and 17I, according to one embodiment, the ejection surface 126 is located in a recess in the link 100, 104. Strategically positioning the ejection surface 126 on a link 100, 104 ensures that the ejection surface 126 does not affect the interaction of one link 100, 104 with another such as by positioning any ejection pin imperfections away from the mating surfaces between adjacent links. Thus, the above-described procedure ensures that each link 100, 104 articulates smoothly relative to another link 100, 104.

Cables

Figure 12B:
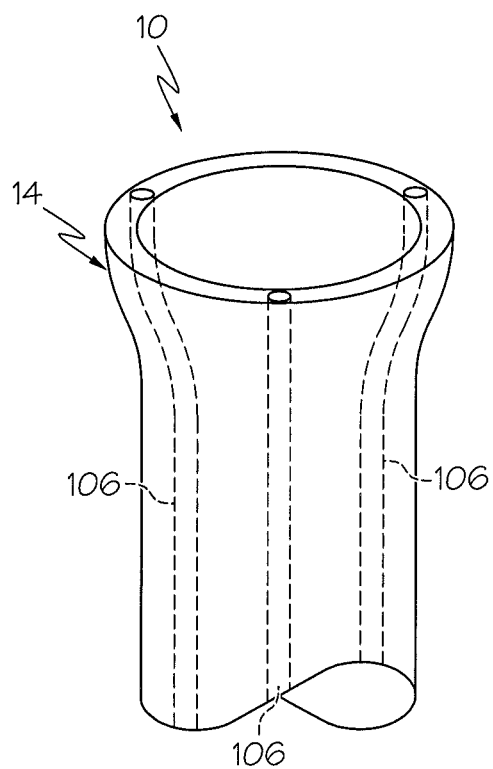

As discussed in the overview above, one or more cables may be used to control the outer links 104 of the outer sleeve 14 and the inner links 100 of the inner core 12. Further examples of cable configurations are described below. In these configurations, as shown in FIG. 12B, a plurality of outer cables 106 can extend through the plurality of outer links 104. The outer cables 106 are configured to control (e.g. steer and transition between flexible and rigid) the outer sleeve 14. In an embodiment, each of the plurality of outer cables 106 has approximately the same tensile strength and/or approximately the same cross-sectional area.

Figure 13B:
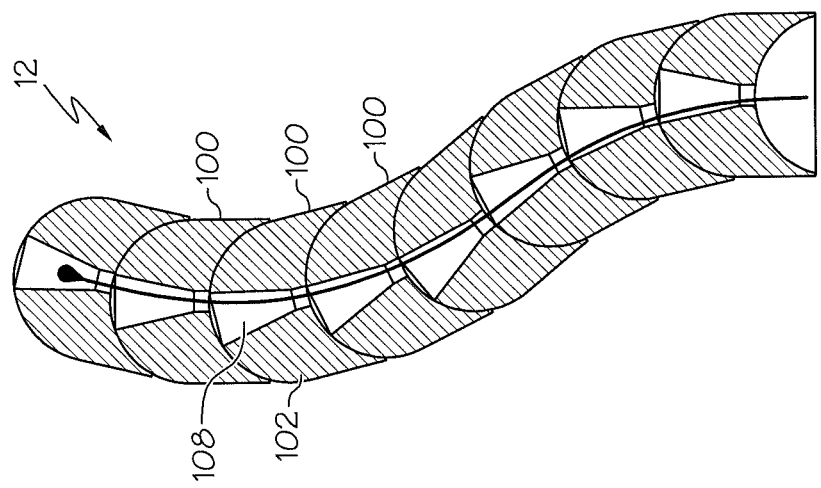
FIGS. 13A-13B illustrate a cross section of an inner core according to an embodiment, in accordance with the present inventive concepts.
Figure 13A:
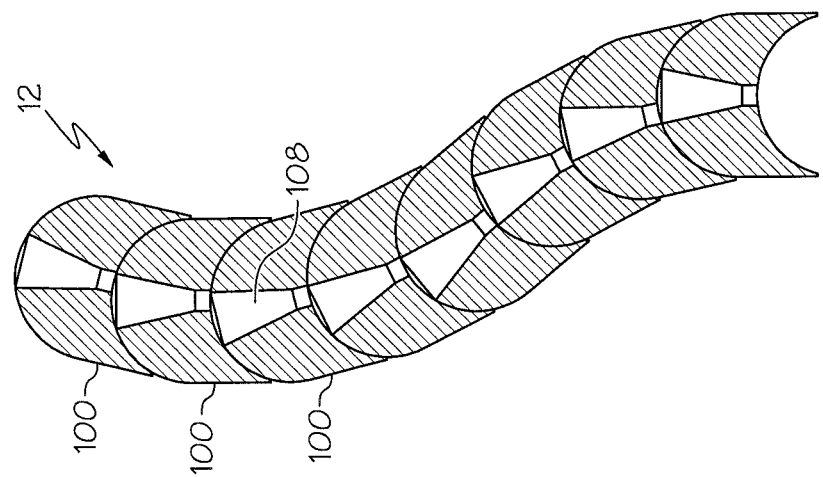

As shown in FIGS. 13A-13B, an inner cable 102 extends through the plurality of inner links 100. The inner cable 102 is configured to control inner core 12 (e.g. transition between flexible and rigid). In an embodiment, the tensile strength and/or cross sectional area of the inner cable 102 is related to the tensile strength and/or cross sectional area of the plurality of outer cables 106.

The relationship between the tensile strength and/or cross sectional area of the inner cable 102 and the plurality of outer cables 106 provide for efficient movement and operation of the articulated probe 10. With regard to tensile strength, the inner cable 102 can have a tensile strength greater than each of the individual outer cables 106. In some embodiments, the tensile strength of the inner cable 102 is approximately equal to a combined tensile strength of the plurality of outer cables 106. In some embodiments, the tensile strength of each of the plurality of outer cables 106 is approximately 1/Nth of a tensile strength of the inner cable 102, where N is the number of outer cables 106. For example, the tensile strength of the inner cable 102 and the combined tensile strength of the outer cables 106 can be in the range of 2-500 lbs, and, in some embodiments, is about 30 lbs.

Figure 13C:
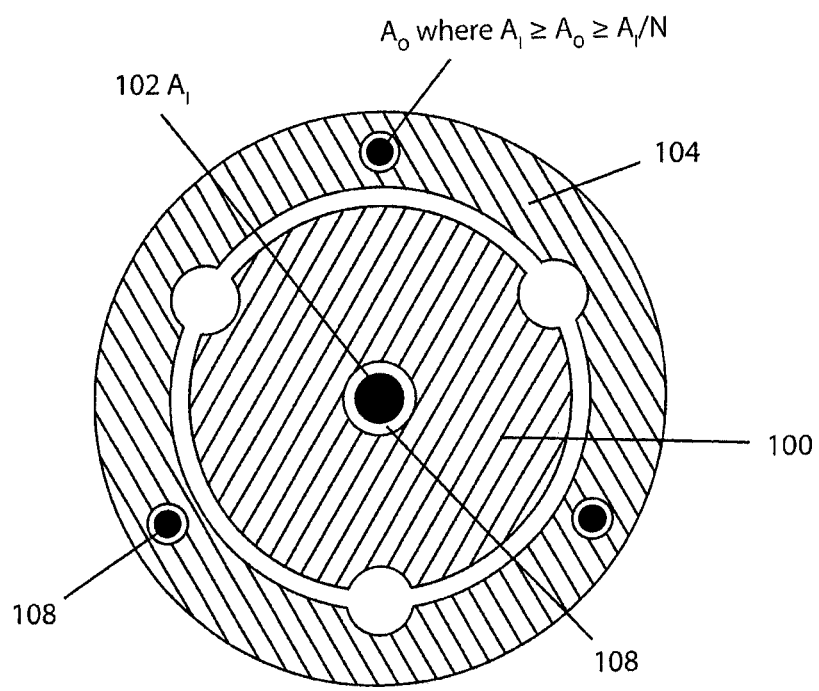
FIG. 13C illustrates a view of an inner link having an inner cable positioned in an outer link having a plurality of outer cables according to an embodiment.

With regard to cross-sectional area, as shown in FIG. 13C, the cross-sectional area ($A_o$) of each of plurality of outer cables 106 can be as small as approximately 1/Nth of a cross-sectional area ($A_i$) of the inner cable 102, where N is the number of outer cables. This relationship is particularly, though not exclusively, important in a configuration where the cables 102, 106 are formed of the same material and/or when the probe 10 diameter is minimized.

The material forming the inner and outer cables 102, 106 can impact the configuration of the cables. The inner cable 102 and the plurality of outer cables 106 may be comprised of the same material, which, in some embodiments, can be at least one of steel, polyethylene (UHMW-ultra-high-molecular-weight), plastic, nylon and fluorocarbons, with steel being more preferred in some embodiments. The inner cable 102 and the plurality of outer cables 106 can be formed from by a monofilament or braided technique. However, the desired tensile strength relationships can also be achieved by using different materials for the inner cable 102 and the outer cables 106.

In sum, the inner cables 102 and outer cables 106 used to control the inner core 12 and outer sleeve 14 can have various characteristics. These characteristics include, but are not limited to the tensile strength, the cross-sectional area and the composition of the cables 102, 106. Configuring the cables based on desired characteristics and relationships with respect to the inner cable 102 and the outer cables 106 determine the stability and other performance parameters of the articulated probe 10.

While the preferred embodiments of the devices and methods have been described in reference to the environment in which they were developed, they are merely illustrative of the principles of the inventive concepts. Modification or combinations of the above-described assemblies, other embodiments, configurations, and methods for carrying out the invention, and variations of aspects of the inventive concepts that are obvious to those of skill in the art are intended to be within the scope of the claims. In addition, where this application has listed the steps of a method or procedure in a specific order, it may be possible, or even expedient in certain circumstances, to change the order in which some steps are performed, and it is intended that the particular steps of the method or procedure claim set forth here below not be construed as being order-specific unless such order specificity is expressly stated in the claim.

We claim:

1. An articulated probe comprising:
   a plurality of outer links configured to pivot relative to one another through a first maximum pivot angle; and
   an elongated member,
   wherein at least two of the plurality of outer links each includes an outer link first portion, an outer link second portion, and a first channel extending through the outer link first and second portions of the outer links,
   wherein a first portion of the first channel in the outer link first portion of each of the at least two of the plurality of outer links is tapered in an amount that permits the plurality of outer links to pivot at the first maximum pivot angle while providing a substantially continuous surface between the first channels of the outer links, respectively,
   wherein the first portion of the first channel of a first outer link of the at least two of the plurality of outer links is positioned in a second portion of the first channel in the outer link second portion of an adjacent second outer link so that an outer surface of the first outer link abuts the second portion of the first channel of the second outer link, and remains only in the second portion of the first channel at the first maximum pivot angle, and
   wherein a greatest width of the tapered first portion of the first channel in the first outer link is greater than a width of an uppermost region of the second portion of the first channel in the second outer link to form a portion of the substantially continuous surface between the first channels of the first and second outer links, respectively, the articulated probe further comprising a plurality of inner links that are structurally different than the outer links and configured to pivot relative to one another through a second maximum pivot angle, the plurality of inner links each comprising a second channel for receiving an elongated member therein, wherein the second channel in each of the inner links is tapered in an amount that permits the inner links to pivot through the second maximum pivot angle while providing a substantially continuous surface between the second channels of the inner links,
   wherein the second maximum pivot angle of the inner links is greater than the first maximum pivot angle of the outer links,
   wherein only the outer links of the inner and outer links have outwardly extending flanges,
   wherein the outer links include at least one distal outer link, and
   wherein a width of the outwardly extending flange of the at least one distal outer link is greater than a width of outwardly extending flanges of other outer links of the outer links.

2. The articulated probe of claim 1, further comprising an inner core comprising the plurality of inner links.

3. The articulated probe of claim 1, further comprising an outer sleeve comprising the plurality of outer links, and wherein the first channel is positioned within at least two of the plurality of outer links.

4. The articulated probe of claim 1, wherein the at least two of the plurality of outer links comprises a side port and a channel is positioned within the side port.

5. The articulated probe of claim 1, wherein the first or second channel comprises a recess in the at least two of the plurality of outer links or inner links.

6. The articulated probe of claim 1, wherein an
   angle of the tapered first portion of the first channel of the first outer link is approximately twice the first maximum pivot angle, and wherein an angle of the tapered second channel of the inner link is approximately twice the second maximum pivot angle.

7. The articulated probe of claim 6, wherein the angle of the tapered first portion of the first channel or the angle of the tapered second channel of the inner link is approximately 26 degrees and the first or second maximum pivot angle is approximately 13 degrees.

8. The articulated probe of claim 1, wherein a diameter of the elongated member is less than a diameter of the first or second channels.

9. The articulated probe of claim 1, wherein the elongated member includes at least one of a tool or a cable.

10. The articulated probe of claim 1, wherein the elongated member comprises another plurality of links that extend through at least one of the inner links or the outer links.

11. The articulated probe of claim 1, wherein the articulated probe has a probe central axis, and comprises:
    an inner core having the plurality of inner links configured to pivot relative to one another and the probe central axis through an inner maximum pivot angle of the second maximum pivot angle; and
    an outer sleeve having the plurality of outer links configured to pivot relative to one another and the probe central axis through an outer maximum pivot angle of the first maximum pivot angle, wherein the inner maximum pivot angle is greater than the outer maximum pivot angle.

12. The articulated probe of claim 11, wherein the plurality of outer links in the outer sleeve includes:
a first outer link with a first central axis that aligns with the probe central axis, the first outer link including an outwardly extending first flange with a first engagement surface extending radially outward relative to the first central axis; and
a second outer link with a second central axis that can align with the probe central axis, the second outer link including an outwardly extending second flange with a second engagement surface extending radially outward relative to the second central axis,
wherein the first outer link and second outer link are configured to permit the first and second outer links to pivot relative to one another and the probe central axis at the outer maximum pivot angle until the first engagement surface engages the second engagement surface.

13. The articulated probe of claim 12, wherein the first engagement surface tapers relative to a line perpendicular to the first central axis.

14. The articulated probe of claim 12, wherein the second engagement surface tapers relative to a line perpendicular to the second central axis.

15. The articulated probe of claim 12, wherein the first engagement surface tapers approximately 6.5° degrees relative to a line perpendicular to the first central axis and the second engagement surface tapers approximately 6.5° degrees relative to a line perpendicular to the second central axis.

16. The articulated probe of claim 11, wherein the outer maximum pivot angle is no greater than approximately 13 degrees.

17. The articulated probe of claim 11, wherein at least one of the plurality of inner links or the plurality of outer links includes channels configured to receive an elongated member therein, wherein the channels are tapered in an amount that permits pivoting at the outer maximum pivot angle while providing a substantially continuous surface between the channels for the elongated member.

18. The articulated probe of claim 1, wherein the second outer link includes a third portion between the first and second portions of the first channel of the second outer link, wherein the first channel further extends through an inner sidewall of the third portion, and wherein the tapered first portion of the first outer link abuts the inner sidewall of the third portion to form the portion of the substantially continuous surface between the channels of the first and second outer links.

19. The articulated probe of claim 1, wherein the inner links have a concave portion, a convex portion, and a uniform linear sidewall extending from the concave portion to the convex portion.

20. An articulated probe with a probe central axis, comprising:
an inner core having a plurality of inner links configured to pivot relative to one another and the probe central axis through an inner maximum pivot angle, wherein the plurality of inner links comprise an inner link channel for receiving an elongated member therein, wherein the inner link channel in each of the inner links is tapered in an amount that permits the inner links to pivot through the inner maximum pivot angle while providing a substantially continuous surface between the inner link channels of the inner links; and
an outer sleeve having a plurality of outer links configured to pivot relative to one another and the probe central axis through an outer maximum pivot angle, wherein the inner links are structurally different than the outer links, wherein only the outer links of the inner and outer links include an outwardly extending flange;
wherein the inner maximum pivot angle of the inner links of the inner core is greater than the outer maximum pivot angle of the outer links of the outer sleeve, wherein at least two links of the outer links each includes a tapered first channel for receiving the inner links and that permits the at least one of the inner links or outer links to pivot at the inner maximum pivot angle or outer maximum pivot angle, respectively, while providing the substantially continuous surface between the tapered first channels of the at least two outer links,
wherein the at least two links of the outer links each includes a plurality of second channels peripheral to the first tapered channel,
wherein the outer links include at least one distal outer link, and
wherein a width of the outwardly extending flange of the at least one distal outer link is greater than a width of outwardly extending flanges of other outer links of the outer links.

21. The articulated probe of claim 20, wherein the plurality of outer links in the outer sleeve includes:
a first outer link with a first central axis that can align with the probe central axis, the first outer link including an outwardly extending first flange with a first engagement surface extending radically outward relative to the first central axis; and
a second outer link with a second central axis that can align with the probe central axis, the second outer link including an outwardly extending second flange with a second engagement surface extending radically outward relative to the second central axis,
wherein the first outer link and second outer link are configured to permit the first and second outer links to pivot relative to one another and the probe central axis at the outer maximum pivot angle until the first engagement surface engages the second engagement surface.

22. The articulated probe according to claim 21, wherein the first engagement surface tapers relative to a line perpendicular to the first central axis.

23. The articulated probe according to claim 21, wherein the second engagement surface tapers relative to a line perpendicular to the second central axis.

24. The articulated probe according to claim 21, wherein the first engagement surface tapers approximately 6.5° degrees relative to a line perpendicular to
the first central axis and the second engagement surface tapers approximately 6.5° degrees relative to a line perpendicular to the second central axis.

25. The articulated probe according to claim 20, wherein the outer maximum pivot angle is no greater than approximately 13 degrees.

26. The articulated probe according to claim 20, wherein the second channels are tapered in an amount that permits pivoting the outer maximum pivot angle while providing a substantially continuous surface between the second channels for the elongated member.

27. An articulated probe comprising:
a plurality of outer links configured to pivot relative to one another through a first maximum pivot angle; and an elongated member, wherein at least two of the plurality of outer links each includes an outer link first portion, an outer link second portion, and a first channel extending through the outer link first and second portions of the outer links, wherein a first portion of the first channel in the outer link first portion of each of the at least two of the plurality of outer links is tapered in an amount that permits the plurality of outer links to pivot at the first maximum pivot angle while providing a substantially continuous surface between the first channels of the outer links, wherein the probe in an articulating state has a first radius of curvature relative to a central axis and a second radius of curvature relative to the central axis that is greater than the first radius of curvature, and wherein the substantially continuous surface includes the tapered first portions of the first channels of the outer links extending along the first radius of curvature, the articulated probe further comprising a plurality of inner links that are structurally different than the outer links and configured to pivot relative to one another through a second maximum pivot angle, the plurality of inner links comprising a second channel for receiving an elongated member therein, wherein the second channel in each of the inner links is tapered in an amount that permits the inner links to pivot through the second maximum pivot angle while providing a substantially continuous surface between the second channels of the inner links, wherein the second maximum pivot angle of the inner links is greater than the first maximum pivot angle of the outer links; and wherein only the outer links of the inner and outer links have outwardly extending flanges of the outer link second portions, wherein the outer links include at least one distal outer link, and wherein a width of the outwardly extending flange of the at least one distal outer link is greater than a width of outwardly extending flanges of other outer links of the outer links.

* * * * *